(12) United States Patent
Kurosawa et al.

(10) Patent No.: US 10,416,165 B2
(45) Date of Patent: Sep. 17, 2019

(54) METHOD FOR PRODUCING ANTIGEN SPECIFIC MONOCLONAL ANTIBODY

(71) Applicant: National University Corporation University of Toyama, Toyama (JP)

(72) Inventors: Nobuyuki Kurosawa, Toyama (JP); Masaharu Isobe, Toyama (JP)

(73) Assignee: NATIONAL UNIVERSITY CORPORATION UNIVERSITY OF TOYAMA (JP)

( * ) Notice: Subject to any disclaimer, the term of this patent is extended or adjusted under 35 U.S.C. 154(b) by 0 days.

(21) Appl. No.: 15/751,792

(22) PCT Filed: Aug. 10, 2016

(86) PCT No.: PCT/JP2016/073664
§ 371 (c)(1),
(2) Date: Feb. 9, 2018

(87) PCT Pub. No.: WO2017/026532
PCT Pub. Date: Feb. 16, 2017

(65) Prior Publication Data
US 2018/0292407 A1    Oct. 11, 2018

(30) Foreign Application Priority Data

Aug. 10, 2015 (JP) ................. 2015-157859

(51) Int. Cl.
| | | |
|---|---|---|
| *C07H 21/02* | (2006.01) | |
| *C07H 21/04* | (2006.01) | |
| *C07K 16/00* | (2006.01) | |
| *A61K 39/00* | (2006.01) | |
| *C07K 14/00* | (2006.01) | |
| *G01N 33/577* | (2006.01) | |
| *C07K 16/18* | (2006.01) | |
| *C12N 1/02* | (2006.01) | |
| *C12N 15/09* | (2006.01) | |
| *G01N 33/53* | (2006.01) | |
| *C07K 16/40* | (2006.01) | |
| *C12N 5/12* | (2006.01) | |
| *C12N 9/50* | (2006.01) | |
| *C12N 11/14* | (2006.01) | |

(52) U.S. Cl.
CPC ........... *G01N 33/577* (2013.01); *C07K 16/18* (2013.01); *C07K 16/40* (2013.01); *C12N 1/02* (2013.01); *C12N 15/09* (2013.01); *G01N 33/53* (2013.01); *C07K 2317/565* (2013.01); *C12N 5/12* (2013.01); *C12N 9/50* (2013.01); *C12N 11/14* (2013.01)

(58) Field of Classification Search
CPC ............ A61K 38/1709; A61K 2300/00; A61K 2039/505; C07K 14/47; C07K 2319/00
See application file for complete search history.

(56) References Cited

U.S. PATENT DOCUMENTS

| | | |
|---|---|---|
| 2011/0020879 A1 | 1/2011 | Isobe et al. |
| 2011/0117609 A1 | 5/2011 | Kurosawa et al. |
| 2013/0023009 A1 | 1/2013 | Kurosawa et al. |
| 2016/0130574 A1 | 5/2016 | Sadekova et al. |

FOREIGN PATENT DOCUMENTS

| | | |
|---|---|---|
| WO | WO2004072286 A1 | 8/2004 |
| WO | WO2005090555 A1 | 9/2005 |
| WO | WO2007062245 A1 | 5/2007 |
| WO | WO2007148417 A1 | 12/2007 |
| WO | WO2009091048 A1 | 7/2009 |
| WO | WO2009110606 A1 | 9/2009 |
| WO | WO2011027808 A1 | 3/2011 |
| WO | WO2011118579 A1 | 9/2011 |

(Continued)

OTHER PUBLICATIONS

Kurosawa et al., "Novel method for the high-throughput production of phosphorylation site-specific monoclonal antibodies", Nature Scientific Reports, 2016, 6:25174:pdf pp. 1-11.*

(Continued)

*Primary Examiner* — Barry A Chestnut
(74) *Attorney, Agent, or Firm* — Mendelsohn Dunleavy, P.C.

(57) ABSTRACT

A method for separating cells capable of producing target antigen-specific monoclonal antibodies (TASMAs) wherein a cell group including antibody-producing cells is immobilized using a reversible crosslinking agent having cell membrane-permeating properties. The immobilized cell group is subjected to cell membrane dissolution using a surface active agent; and the cell group is reacted with a labeling target antigen. In the stained cell group a that has reacted with the labeling target antigen is separated. A method to produce TASMAs by separating mRNA from the cell separated using the method; preparing cDNA and preparing antigen-specific monoclonal antibodies or fragments thereof from the prepared cDNA. Also provided are a method whereby at least one cell capable of producing TASMAs is separated and a method whereby said antibodies can be produced by using the separated cell. Threonine 18 phosphorylated p53 (pT18-p53) and threonine 68 phosphorylated CHK2 (pT68-CHK2) specific monoclonal antibodies are also disclosed.

17 Claims, 12 Drawing Sheets

Specification includes a Sequence Listing.

(56) References Cited

FOREIGN PATENT DOCUMENTS

WO    WO2012133572 A1    10/2012

OTHER PUBLICATIONS

Kurosawa et al., "Rapid production of antigen-specific monoclonal antibodies from a variety of animals", BMC Biol., 2012, 10(80):1-14.*
Macherey, N., "RNA isolation from FFPE Samples User Manual Nucleospin FFPE RNA", internet 2010, pdf pp. 1-33.*
European Office Action; dated Aug. 14, 2018 for EP Application No. 16835229.2.
International Search Report; dated Nov. 8, 2016 for PCT Application No. PCT/JP2016/073664.
Kurosawa, N., et al. "Rapid production of antigen-specific monoclonal antibodies from a variety of animals." BMC biology 10.1 (2012): 80.
Kuhne, M., et al. "Comparative characterization of mAb producing hapten-specific hybridoma cells by flow cytometric analysis and ELISA." Journal of immunological methods 413 (2014): 45-56.
Kurosawa, N., et al. "Novel method for the high-throughput production of phosphorylation site-specific monoclonal antibodies." Scientific reports 6 (2016): 25174.
International Preliminary Report on Patentability; dated Jul. 25, 2017 for PCT Application No. PCT/JP2016/073664.
Diez, C., et al., "Isolation of full-size mRNA from cells sorted by flow cytometry." Journal of biochemical and biophysical methods 40.3 (1999): 69-80.
Tiller, T., et al., "Efficient generation of monoclonal antibodies from single human B cells by single cell RT-PCR and expression vector cloning." Journal of immunological methods 329.1-2 (2008): 112-124.
Tiller, T., et al., "Cloning and expression of murine Ig genes from single B cells." Journal of immunological methods 350.1-2 (2009): 183-193.
Jin, A., et al. "Rapid isolation of antigen-specific antibody-secreting cells using a chip-based immunospot array." Nature protocols 6.5 (2011): 668.
"RNA and DNA Isolation from FFPE Samples User Manual: NucleoSpin FFPE RNA/DNA," Jul. 2010/Rev. 02, Macherey-Nagel, 46 pages.
Hrvatin, S., et al. "MARIS: method for analyzing RNA following intracellular sorting." PloS one 9.3 (2014): e89459.
European Search Report; dated Apr. 12, 2018 for EP Application No. 16835229.2.
Communication pursuant to Article 94(3) EPC for Application No. 16 835 229.2; dated Feb. 4, 2019.
Communication pursuant to Article 94(3) EPC for European patent application No. 16835229.2; dated Jun. 13, 2019.

* cited by examiner paired amplification 79/96 (83%)

METHOD FOR PRODUCING ANTIGEN SPECIFIC MONOCLONAL ANTIBODY

TECHNICAL FIELD

The present invention relates to a method for separating a cell capable of producing a monoclonal antibody with specificity toward an antigen of interest and a method for producing a monoclonal antibody with specificity toward an antigen of interest using the cell separated by the separation method.

CROSS-REFERENCE OF RELATED APPLICATION

This application claims the priority of Japanese Patent Application No. 2015-157859 filed on Aug. 10, 2015, which is hereby specifically incorporated by reference in their entirety.

BACKGROUND ART

Antibodies are molecules in the center of biological defense and have been an important tool used in research and diagnosis. In more recent years, novel therapeutic agents, i.e. antibody drugs utilizing antibodies as medicaments, have shown remarkable therapeutic effects. In order to obtain novel antibodies that can be used as medicaments and the like in a rapid and secure manner, it is required to establish a production platform by introducing novel techniques.

Many of the functional antigen epitopes of human proteins which are targeted by antibody drugs have low antigenicity in mice. Therefore, sufficient immune reaction is not triggered even when the antigens are inoculated to mice, and thus it is not easy to obtain antibodies toward such antigens with antigen epitopes having low antigenicity in mice. Therefore, there is a need for a technique that allows efficient production of antibodies in animals other than mice having high immunogenicity towards human antigens.

Meanwhile, when obtaining a recombinant monoclonal antibody from immunized animals by genetic engineering means, a method is used in which antigen specific single plasma cells are separated. Proposed methods for separating antigen specific single plasma cells include those in which an antibody secreted from the single plasma cells is used and in which an antibody expressed on the single plasma cells is used.

PTL 1 discloses a fluorescent probe for identifying or isolating plasma cells and a method for identifying or isolating plasma cells using the probe. PTL 2 discloses a method for producing an antibody with specificity toward an antigen of interest from plasma cells isolated by the method described in PTL 1.

NPL 1 discloses efficient generation of monoclonal antibodies from single human B cells by single cell RT-PCR and expression vector cloning.

NPL 2 discloses cloning and expression of murine IgGenes from single human B cells.

NPL 3 discloses rapid isolation of antigen-specific antibody-secreting cells using a chip-based immunospot array.

PRIOR ART REFERENCES

Patent Document

PTL 1: WO2011/118579 (PCT/JP2011/56831)
PTL 2: WO2012/133572 (PCT/JP2012/058216)

Non-Patent Documents

NPL 1: Thomas Tiller et al., Journal of Immunological Methods 329 (2008) 112-124
NPL 2: Thomas Tiller et al., Journal of Immunological Methods 350 (2009) 183-193
NPL 3: Jin A et al., Nat Protoc. (2011) 6(5) 668-76
NPL 4: Kurosaw et al., BMC Biol. (2012) 10:80
NPL 5: Isolation of full-size mRNA from cells sorted by flow cytometry (J Biochem Biophys Methods, 1999)
NPL 6: MARIS: Method for Analyzing RNA following Intracellular Sorting (PLOS one, 2014)

The entire disclosures of PTLs 1 and 2 and NPLs 1 to 6 are expressly incorporated herein by reference.

SUMMARY OF THE INVENTION

The method disclosed in PTL 1 allows separation of plasma cells from various animals. However, according to the study carried out by the inventors of the present invention, it was difficult to separate antigen specific plasma cells from other plasma cells with high accuracy. Therefore, according to the method disclosed in PTL 2 which utilizes the method disclosed in PTL 1, an antibody with specificity toward an antigen of interest could not be efficiently prepared.

The methods disclosed in NPL 1 and 2 are mouse and human monoclonal antibody preparation methods utilizing recombinant DNA techniques. However, the methods could not be applied to animal species other than mice and humans. Further, the methods also have issues of incapability of selection of antigen specific clones.

The method disclosed in NPL 3 allows selection of antigen specific clones in mice and humans. However, selection of antigen specific clones requires preparation of complicated devices and also requires a preliminary treatment which is concentration of plasma cells.

The method disclosed in NPL 4 allows selection of antigen specific clones from various animals. However, antibodies secreted from single cells and antibodies expressed on the membrane are only a minute amount. Therefore, the method for separating antigen specific plasma cells which utilizes a signal resulting from binding of a labelled antigen to the antibody molecules still has many issues in terms of both accuracy and sensitivity. When the content of antigen specific plasma cells in a cell population is 0.01% or less, it also causes a problem that antigen specific clones cannot be selected with high accuracy.

Thus, an object of the present invention is to provide a method that allows separation of at least one single cell capable of producing a monoclonal antibody with specificity toward an antigen of interest with high accuracy from various animals without requiring complicated methods, and to provide a method that allows production of a monoclonal antibody with specificity toward an antigen of interest with high accuracy from various animals without requiring complicated methods by using at least one single cell separated by the above method. Another object of the present invention is to provide a novel monoclonal antibody with specificity toward an antigen of interest.

Solution to the Problem

It is known that antibody-producing cells contain in the cytoplasm thereof at least 1000 times greater antibodies than the antibodies expressed on the membrane (NPL 4). The inventors of the present invention focused on this point and assumed that the signal obtained by binding of a labelled antigen to antibodies in the cytoplasm may be much stronger than the signal obtained by binding of a labelled antigen to membrane-bound antibodies. However, it was assumed that in order to actually allow binding of an antigen to antibodies in the cytoplasm, preliminary treatments are required such as fixing of proteins with a crosslinking reagent and cell membrane permeation treatment with a detergent. However, it is predicted that such preliminary treatments may highly likely cause intermolecular crosslinking between proteins and mRNA or degradation of RNA due to nucleases in the cytoplasm. Therefore, it has been thought to be very difficult to extract mRNA from single cells which have undergone fixation with a crosslinking reagent, membrane permeation with a detergent and staining with a labelled antigen and to amplify gene fragments with 250 bp or more in length from the extracted mRNA (NPL 5 and 6).

Under such circumstances, the inventors of the present invention carried out various examinations in order to break through the difficult situation. During the examinations, the inventors of the present invention developed a novel procedure for preparing an antigen specific monoclonal antibody by identifying and separating an antigen specific plasma cell from a cell population which has undergone fixing of cells with a reversible crosslinking reagent, treatment for membrane permeation and staining with a labelled antigen, and cloning immunoglobulin variable region genes from the plasma cell, thereby completing the present invention.

Thus, the present invention is as follows.

[1] A method for isolating a cell capable of producing a monoclonal antibody with specificity toward an antigen of interest, wherein the method comprises the following steps;
 (1) fixing a cell population containing antibody-producing cells with a crosslinking reagent, wherein the crosslinking reagent is a reversible crosslinking regent having the cell membrane permeability (a fixing step);
 (2) treating the fixed cell population with a detergent (a cell membrane lysis step);
 (3) reacting the cell membrane lysed cell population with a labelled antigen of interest (a staining step); and
 (4) isolating at least one single cell which has been reacted with the labelled antigen of interest from the cell population that underwent the staining step,
wherein the cell membrane lysis step (2) and the staining step (3) can be carried out sequentially or in parallel.

[2] The method according to [1], wherein the crosslinking reagent is formalin or a bivalent crosslinking reagent having an S—S bond in a spacer chain.

[3] The method according to [1] or [2], wherein the detergent is at least one detergent selected from the group consisting of a nonionic detergent, an amphoteric detergent and an ionic detergent.

[4] The method according to [1] or [2], wherein the detergent is a nonionic detergent.

[5] The method according to any one of [1] to [4], wherein at least one step of steps (1) to (4) is carried out in the presence of an RNase inhibitor.

[6] A method for producing a monoclonal antibody with specificity toward an antigen of interest, the method comprises the following steps:
 (5) preparing a cDNA by separating mRNA from the at least one cell isolated by the method of any one of [1] to [5] (a cDNA preparing step); and
 (6) preparing the antigen specific monoclonal antibody or fragment thereof from the cDNA obtained in the cDNA preparing step (a preparing step of the monoclonal antibody specific to an antigen of interest).

[7] The method according to [6], wherein at least step (5) is carried out in the presence of an RNase inhibitor.

[8] The method according to [6] or [7], wherein the mRNA separation is performed on equal to or less than 10 of the isolated antibody producing cells.

[9] The method according to any one of [6] to [8], wherein a primer having a sequence corresponding to a region around the initiation codon of an immunoglobulin of interest is used as a sense primer of the second PCR used for a cDNA synthesis in the cDNA preparation of step (5).

[10] The method according to any one of [6] to [9], wherein the mRNA separation of step (5) comprises a decrosslinking treatment of the isolated cell.

[11] The method according to [10], wherein the decrosslinking treatment is a heating treatment if the crosslinking reagent is formalin.

[12] The method according to [11], wherein the heating treating is carried out in the present of protease to obtain fragments of variable region genes of antibody gene.

[13] The method according to [10], wherein the decrosslinking treatment is a reduction treatment if the crosslinking reagent is a bivalent crosslinking reagent having an S—S bond in a spacer chain.

[14] A monoclonal antibody specific to threonine 18-phosphorylated p53 (pT18-p53) having a gamma chain comprising a variable region having an amino acid sequence shown in SEQ ID NO: 9 and a kappa chain comprising a variable region having an amino acid sequence shown in SEQ ID NO: 10.

[15] A monoclonal antibody specific to threonine 18-phosphorylated p53 (pT18-p53) having a gamma chain comprising CDR1, CDR2 and CDR3 having amino acid sequences shown in SEQ ID NOs: 3 to 5, respectively, and a kappa chain comprising CDR1, CDR2 and CDR3 having amino acid sequences shown in SEQ ID NOs: 6 to 8, respectively.

[16] A monoclonal antibody specific to threonine 68-phosphorylated CHK2 (pT68-CHK2) having a gamma chain comprising a variable region having an amino acid sequence as shown in SEQ ID NO: 17 and a kappa chain comprising a variable region having an amino acid sequence as shown in SEQ ID NO: 18.

[17] A monoclonal antibody specific to threonine 68-phosphorylated CHK2 (pT68-CHK2) having a gamma chain comprising CDR1, CDR2 and CDR3 having amino acid sequences shown in SEQ ID NOs: 11-13, respectively, and a kappa chain comprising CDR1, CDR2 and CDR3 having amino acid sequences shown in SEQ ID NOs: 14-16, respectively.

According to the present invention, at least one single cell capable of producing a monoclonal antibody with specificity toward an antigen of interest can be separated (hereinafter, separation of at least one single cell may also be referred to as isolation of a cell) with high accuracy without limitation by the animal species used for immunization or without using a complicated method, and the present invention can provide a method allowing preparation of a monoclonal antibody with specificity toward an antigen of interest by using the isolated cell. As a result, the present invention enables development of antibody drugs and diagnostic drugs toward a molecule of interest, which otherwise have been difficult to prepare with existing techniques. According to the present invention, novel monoclonal antibodies specific to threonine 18-phosphorylated p53 (pT18-p53) and to threonine 68-phosphorylated CHK2 (pT68-CHK2) are provided.

DESCRIPTION OF EMBODIMENT

Figure 1A:
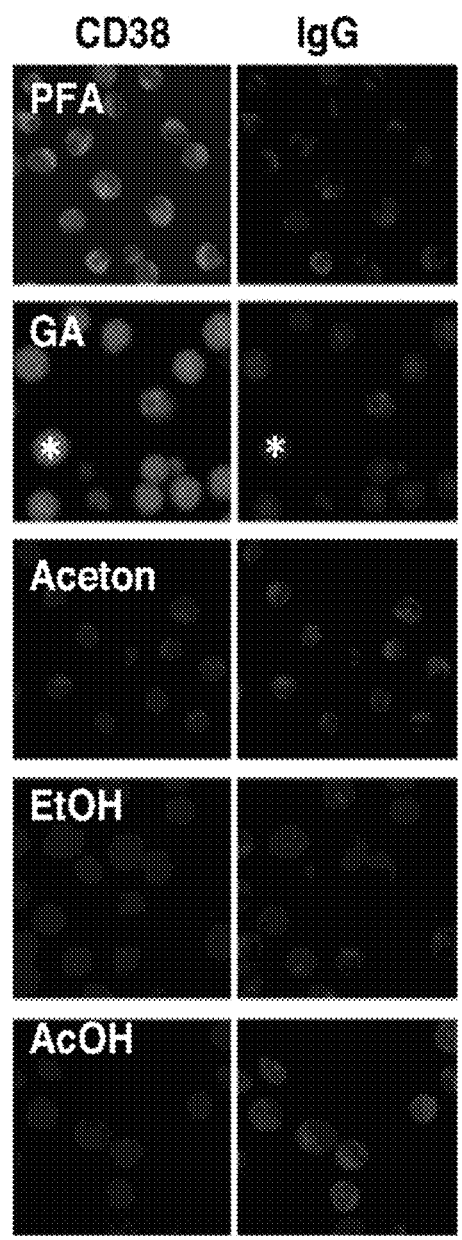
FIG. 1A shows fluorescence micrographs of Example 1 (A).

The method for isolating a cell capable of producing a monoclonal antibody with specificity toward an antigen of interest of the present invention comprises the following steps (1) to (4):

(1) fixing a cell population containing antibody-producing cells with a crosslinking reagent, wherein the crosslinking reagent is a reversible crosslinking regent having the cell membrane permeability (a fixing step);

(2) treating the fixed cell population with a detergent (a cell membrane lysis step);

(3) reacting the cell membrane lysed cell population with a labelled antigen of interest (a staining step), wherein the cell membrane lysis step (2) and the staining step (3) can be carried out sequentially or in parallel; and (4) isolating at least one single cell which has been reacted with the labelled antigen of interest from the cell population that underwent the staining step (a cell isolation step).

Further, the method for producing a monoclonal antibody with specificity toward an antigen of interest of the present invention includes the following steps (5) and (6):

(5) preparing a cDNA by separating mRNA from the at least one cell isolated by the cell isolation method of the present invention (a cDNA preparing step); and (6) preparing the antigen specific monoclonal antibody or a fragment thereof from the cDNA obtained in the cDNA preparing step (a preparing step of the monoclonal antibody specific to the antigen of interest).

<Method for Isolating a Cell Producing a Monoclonal Antibody with Specificity Toward an Antigen of Interest>

(1) Fixing Step

In the fixing step, a cell population containing antibody-producing cells is subjected to fixing with a crosslinking reagent. The fixing treatment is to fix antibodies (such as IgG, IgA, IgM, IgD, IgE and IgY) in the antibody-producing cells and mRNA of the antibodies. Various methods are known for fixing biological substances including cells. In the present invention, antibodies and mRNA thereof in the antibody-producing cells are fixed, so that elution of the antibodies and mRNA thereof in the cells in the next detergent treatment step accompanying lysis of the cell membrane is suppressed. The antibodies in the cells are used for identification of antibody-producing cells using a labelled antigen of interest in the later step. Therefore, it is preferable that antibodies in the cells can remain in the cells after lysis of the cell membrane by fixing the antibodies in the cells and it is preferable that the antibodies are fixed in the state that the antibodies are capable of reacting with a labelled antigen of interest. mRNA of antibodies fixed in the cells after lysis of the cell membrane is used for cDNA synthesis in the later step. Prior to cDNA synthesis, fixed mRNA of the antibodies is defixed. Therefore, it is preferable to fix mRNA of the antibodies so that the mRNA can be used for cDNA synthesis after defixing, and that a method for defixing the fixed mRNA of antibodies is available, and preferably defixing can be easily carried out. The fixation treatment which fulfils such requirements is a method in which formalin or a bivalent crosslinking reagent having an S—S bond in a spacer chain is used. The details of the method are described hereinafter.

The cell population containing antibody-producing cells is obtained by immunizing an animal with an antigen of interest and collecting cells from the immunized animal. The manner of immunizing an animal with an antigen of interest and collecting a cell population containing antibody-producing cells from the immunized animal may be divided into two methods, one of which is a method (hereinafter referred to as the NHA method) in which a subject is a non-human animal and the other is a method (hereinafter referred to as the HU method) in which a subject is human. The NHA method in which a subject is a non-human animal includes collecting cells derived from the lymph fluid, lymph tissue, blood cell sample or bone marrow from a non-human animal and sensitizing in vitro the collected cells derived from the lymph fluid, lymph tissue, blood cell sample or bone marrow with an antigen of interest, or immunizing the non-human animal with an antigen of interest and collecting cells derived from the lymph fluid, lymph tissue, blood cell sample or bone marrow from the animal after establishment of the immunity. According to the NHA method, a cell population containing antibody-producing cells of a non-human animal which specifically bind to an antigen of interest can be obtained.

The HU method in which a subject is human includes collecting cells derived from the lymph fluid, lymph tissue, blood cell sample or bone marrow from the subject and sensitizing in vitro the collected cells derived from the lymph fluid, lymph tissue, blood cell sample or bone marrow with an antigen of interest, or collecting cells derived from the lymph fluid, lymph tissue, blood cell sample or bone marrow from the subject having an antibody toward an antigen of interest. According to the HU method, a cell population containing antibody-producing cells of the subject which specifically bind to an antigen of interest can be obtained.

<Immunization of a Non-Human Animal with an Antigen of Interest>

The NHA method is hereinafter described.

A non-human animal is immunized with an antigen of interest. The term "non-human animal" as used herein means any animal having an immune system other than humans. Examples of the animal include mammals and birds. Examples of mammals include apes, monkeys, dogs, cats, horses, cows, pigs, sheep, goats, donkeys, camels, llamas, alpacas, reindeers, buffaloes, yaks, guinea pigs, rabbits, minks, mice, rats, sand rats, hamsters, golden hamsters, Armenian hamsters, ferrets, miniature pigs, racoons, possums, Suncus, kangaroos, dolphins and the like. Examples of birds include chickens, quails, ostrich and the like.

The terms "an antigen of interest" as used herein refers to microorganisms such as viruses, mycoplasmas, bacteria and fungi, Lophotrocozoa such as shellfish, Ecdysozoa such as insects and crustaceans, Deuterostomia such as vertebrates and constituents thereof, proteins, saccharides, lipids, glycoconjugates, nucleic acids, natural low molecular organic compounds, natural polymeric organic compounds, artificial low molecular organic compounds, artificial polymeric organic compounds, metal complexes and the like. It should be noted that the foregoing does not limit the type of the antigen of interest and is merely examples.

The antigen of interest used for immunization of a non-human animal may be the antigen of interest per se, or an organism containing the antigen of interest or a dead organism or an extract of the organism, or a product obtained after binding to or mixing with an appropriate carrier.

The cells derived from the lymph fluid, lymph tissue, blood cell sample or bone marrow are collected from the non-human animal and the collected cells derived from the lymph fluid, lymph tissue, blood cell sample or bone marrow are sensitized in vitro with the antigen of interest. Sensitization of the lymph fluid and the like in vitro with the antigen of interest may be carried out as described below. Antigen presenting cells including dendritic cells, T cells and B cells are collected from a non-human animal. In a test tube, the antigen is allowed to work on dendritic cells for phagocytosis and digestion, thereby preparing mature dendritic cells now possessing an ability of presenting the antigen. To the cells, T cells, B cells and an immune stimulating agent such as a cytokine including interleukin 2 or poly(dI-dC) are added, and B cells responding to the antigen are grown and differentiated in a test tube, resulting in a cell population containing antibody-producing cells.

The phrase "immunize a non-human animal with an antigen of interest" or the like as used herein means to bring an antigen of interest into contact with a non-human animal to allow manifestation of immunity against the antigen of interest in the non-human animal. The manner for allowing manifestation of immunity against an antigen of interest is not particularly limited and may be, for example, administration or implantation of an antigen of interest to a non-human animal, thereby immunizing the non-human animal. The manner of administration or implantation of an antigen of interest is not particularly limited. Examples of the manner of administration include intratracheal administration, oral administration, subcutaneous injection, intravenous injection, intramuscular injection and gene transfer into a non-human animal to express an antigen in the animal body. Alternatively, a non-human animal may be immunized by bringing an antigen of interest into contact with the skin of the non-human animal.

Immunization of a non-human animal with an antigen of interest is carried out until the immunity against the antigen of interest is established in the non-human animal. Therefore, the antigen of interest is brought into contact with the non-human animal until the immunity against the antigen of interest is established. The frequency and period of the contact of the antigen of interest with the non-human animal and the amount of the antigen of interest per dose may be appropriately selected according to an ease of establishment of the immunization. Whether or not the immunity against the antigen of interest is established in the non-human animal maybe verified according to a conventional method such as ELISA for measuring antibodies in the serum after collection of blood from the non-human animal.

<Collection of the Lymph Node and the Like From Animals After Establishment of the Immunity>

From the animal after establishment of the immunity, cells derived from the lymph fluid, lymph tissue, blood cell sample or bone marrow are collected. As an object of the present method is to collect the cell population containing antibody-producing cells of a non-human animal that specifically bind to the antigen of interest, cells derived from the lymph fluid, lymph tissue, blood cell sample or bone marrow which are likely to contain the cell population containing antibody-producing cells are collected.

The lymph fluid, lymph tissue, blood cell sample or bone marrow may be prepared, for example, as follows. From a non-human animal to which an antigen was injected subcutaneously, intramuscularly or at a pad on or before about one month ago, the swollen lymph tissue is removed with the lymph fluid by surgery. The tissue attached to the lymph node is eliminated under a stereoscopic microscope followed by breaking the membrane of the lymph node with forceps, thereby dispersing cells in the lymph node into a PBS solution (10 mM phosphate buffer, 120 mM NaCl, 2.7 mM KCl, pH 7.6) . The blood cell sample is mononuclear cells which are separated by density gradient centrifugation of the blood collected by heparin blood sampling from an immunized animal. The bone marrow is bone marrow cells obtained by cutting both bone ends of a femur removed from an immunized animal and injecting the PBS solution from one bone end through a syringe needle inserted therein, thereby draining the bone marrow cells from the other bone end. Accordingly, the cell population containing antibody-producing cells may be collected.

<Cell Fixing Treatment with a Crosslinking Reagent>

As described above, the cell population containing antibody-producing cells is treated with a crosslinking reagent which is formalin or a bivalent crosslinking reagent having an S—S bond in a spacer chain to fix antibodies and mRNA thereof in the antibody-producing cells. When cells are subjected to a preliminary treatment for fixing proteins using a crosslinking reagent such as glutaraldehyde with the purpose of fixing antibodies and mRNA in the cells, proteins constituting the cells are fixed. However, as glutaraldehyde is an irreversible crosslinking reagent, antibodies and mRNA in the cells are degenerated. Contrary to this, the crosslinking reagent used in the present invention is a reversible crosslinking reagent having the cell membrane permeability. Because of the cell membrane permeability, antibodies and mRNA in the cells may be intracellularly fixed and the reversible crosslinking reagent is used, so that mRNA can be decrosslinked to allow preparation of cDNA in the stage of cDNA preparation from mRNA which is the later step. Examples of such a reversible crosslinking reagent include formalin and a bivalent crosslinking reagent having an S—S bond in a spacer chain. Examples of the bivalent crosslinking reagent having an S—S bond in a spacer chain include dithiobis [succinimidyl propionate] (DSP) and the like.

When the collected cell population containing antibody-producing cells is subjected to the treatment using the reversible crosslinking reagent, antibodies and mRNA thereof in the cells are fixed in the cells without substantial degeneration (while being able to be decrosslinked). Antibodies are fixed while having a reactivity with a labelled antigen of interest, and mRNA of the antibodies may be decrosslinked and used for cDNA synthesis in the later step. The extent of fixing varies according to the type and concentration of the reversible crosslinking reagent and the temperature and time of the treatment. By changing the type and concentration of the reversible crosslinking reagent and the temperature and time of the treatment according to the type of the antibody-producing cells used, an optimal fixation may result. Fixing may be carried out, for example, under such conditions that the collected cell population containing antibody-producing cells are immersed in an aqueous solution such as phosphate buffered saline (PBS) containing 1% to 10% reversible crosslinking reagent at a temperature in the range of 0° C. to 30° C. or preferably 0° C. to 10° C. for 1 to 60 minutes (the collected cell population containing antibody-producing cells are dispersed in a reversible crosslinking reagent-containing aqueous solution). According to the conditions, antibodies and mRNA thereof may be fixed under a good condition (without substantial degeneration). The thus obtained fixed cell population is preferably separated from the solution by centrifugation and the like and used in the next step.

(2) Cell Membrane Lysis Step

In the cell membrane lysis step, the cell population treated in the fixing step is subjected to a lysis treatment in order to make pores on the cell membrane. Specifically, the cell population which is fixed in the fixing step is mixed with a solution containing a detergent. By mixing with the detergent-containing solution, the cell membrane is lysed and pores are made on the cell membrane. The pores facilitate entrance of a labelled antigen of interest into the cells in the next step and also facilitate transfer of substances from and to the cells during cDNA synthesis from mRNA in the later step. The lysis of the cell membrane in this step is sufficient if pores serving the purpose are formed on the cell membrane and is appropriate if the treatment can provide the cell membrane which has the strength enduring the cell identification and isolation which follow even after being subjected to the lysis of the cell membrane. For this purpose, a detergent is used in the present invention. The type and concentration of the detergent may be appropriately selected by taking the above purpose into account.

The detergent may be at least one detergent selected from the group consisting of nonionic detergents, amphoteric detergents and ionic detergents.

Examples of the nonionic detergent include polyoxyethylene alkyl ethers (including Triton), sorbitan fatty acid esters (including Tween), alkyl polyglucosides, fatty acid diethanolamides, alkyl monoglyceryl ethers and the like. Specific examples of the polyoxyethylene alkyl ether nonionic detergent include Triton X-100 (octylphenol poly (ethylene glycol ether)$_n$ (wherein n is about 10), HLB: 13.4 to 13.5). Specific examples of the fatty acid sorbitan ester nonionic detergent include Tween 20 (Polysorbate 20, polyoxyethylene sorbitan monolaurate, HLB: 16.7). Tween 20 is a polysorbate and polysorbates are sorbitan fatty acid esters condensed with about 20 molecules of ethylene oxide. In addition to Tween 20, mention may be made to Tween 40 (Polysorbate 40, polyoxyethylene sorbitan monopalmitate, HLB 15.6), Tween 60 (Polysorbate 60, polyoxyethylene sorbitan monostearate, HLB 14.9), Tween 65 (Polysorbate 65, polyoxyethylene sorbitan tristearate, HLB 10.5), Tween 80 (Polysorbate 80, polyoxyethylene sorbitan oleate, HLB 15.0), n-dodecyl β-D-maltoside, digitonin, saponin and the like.

Examples of the amphoteric detergent include CHAPS, 3-(N,N-dimethyloctylammonio) propane sulphonate, N-dodecyl-N,N-dimethyl-3-ammonio-1-propane sulphonate, 3-(N,N-dimethyloctadecylammonio) propane sulphonate and the like. The amphoteric detergents are known to rarely destroy the conformation of proteins and may be used for lysis of the membrane similarly to the nonionic detergent.

The ionic detergent may be at least one ionic detergent selected from the group consisting of cholic acid derivatives. Examples of at least one ionic detergent selected from cholic acid derivatives include an anionic detergent such as a cholic acid alkali metal salt (such as sodium cholate) and digoxigenin which is a cholic acid derivative (modified at an alkylene carboxyl group). The ionic detergents are known to rarely destroy the conformation of proteins and may be used for lysis of the membrane similarly to the nonionic detergent.

The concentration of the detergent may be, for example, in the range of 0.1% to 5% according to the type of the detergent, the type of the cells and treatment conditions (temperature and time). The size of the pores formed on the cell membrane may be appropriately controlled by the type and concentration of the detergent and the treatment conditions (temperature and time). The treatment conditions (temperature and time) may be, for example, immersion at a temperature in the range of 0° C. to 30° C., preferably 10° C. to 25° C. for 1 to 60 minutes in a solution (such as a phosphate buffered aqueous solution) containing the detergent. The cell membrane lysis step may, as described hereinbelow, precede the following reaction step with a labelled antigen of interest or may be carried out in parallel with the reaction step with a labelled antigen of interest in the same solution.

(3) Staining Step

In the step, the cell population which has undergone the lysis treatment in the cell membrane lysis step and a labelled antigen of interest are mixed to allow reaction of antibodies in the cells and the labelled antigen of interest. When the cell membrane lysis step and the staining step are carried out in parallel, the cell population obtained in the fixing step is subjected to the treatment with a detergent and the reaction with a labelled antigen of interest in the same solution.

The antigen of interest in the labelled antigen of interest is a substance having an epitope identical to the antigen of interest used for immunization of the non-human animal or the like. Therefore, the labelled antigen of interest and the antigen of interest used for immunization may be completely the same or may be different substances containing the same epitope.

The label of the antigen of interest is not particularly limited as far as the label allows identification and separation of cells reacted with the labelled antigen of interest. Examples of the label include a fluorescence label, a magnetic bead label and the like. The type of the fluorescence label is not particularly limited. The antigen of interest may be appropriately labelled by a well-known method according to the type of the label used.

The cell population obtained in the cell membrane lysis step and the labelled antigen of interest may be allowed to react by, for example, bringing the cell population and the labelled antigen of interest into contact in an aqueous solution such as phosphate buffered saline (PBS). The concentrations of the cell population and the labelled antigen of interest in the aqueous solution, temperature and time may be appropriately selected while confirming the progress of the reaction. The treatment conditions (temperature and time) may be, for example, immersion at a temperature in the range of 0° C. to 30° C. or preferably 0° C. to 10° C. for 1 to 60 minutes in a solution (such as a phosphate buffered aqueous solution) containing the labelled antigen of interest.

When the cell population obtained after fixing is subjected in parallel to the cell membrane lysis treatment and the reaction with the labelled antigen of interest, the cell population is brought into contact with the detergent for cell lysis and the labelled antigen of interest in, for example, an aqueous solution such as phosphate buffered saline (PBS). The concentrations of the cell population, the detergent and the labelled antigen of interest in the aqueous solution, temperature and time may be appropriately selected by confirming the progress of the reaction. The treatment conditions (temperature and time) may be, for example, immersion at a temperature in the range of 0° C. to 30° C. or preferably 0° C. to 10° C. for 1 to 60 minutes in a solution (such as a phosphate buffered aqueous solution) containing the detergent and the labelled antigen of interest.

(4) Cell Isolation Step

In the step (4), at least one single cell which is reacted with the labelled antigen of interest is separated as a single cell. The cells reacted with the labelled antigen of interest are first identified by using the label of the labelled antigen of interest as a guide and identified single cells are separated.

In the method of the present invention, antibodies and mRNA thereof in the cells are fixed in the step (1) and the fixed cell population is treated with the detergent to make pores on the cell membrane in the step (2). Therefore, the labelled antigen of interest can easily enter the cells producing antibodies toward the antigen of interest through the pores on the cell membrane. The labelled antigen of interest binds to the antibody in the cells which are fixed and subjected to the cell membrane lysis treatment and allows identification of cells containing the labelled antigen of interest bound to antibodies. The cells which retain the labelled antigen of interest therein are highly possible to be antibody-producing cells because it is highly possible that the labelled antigen of interest binds to antibodies in the cells.

The cells identified with the label of the labelled antigen of interest as a guide are separated as single cells. Separation of the identified antibody-producing cells may be carried out with, for example, a cell sorter. Separation of single antibody-producing cells by using a cell sorter may be carried out according to a well-known method. Cells may be selected and separated as a cell population including more than one cell or, preferably, each cell is individually selected and separated. The cells selected are highly possible to exhibit a binding ability to the antigen of interest. However, the cells may not always have an identical antibody toward the antigen of interest and it is expected that the amino acid sequences in the antigen-binding sites of the antibodies vary. Therefore, it is possible to obtain different monoclonal antibodies which specifically bind to the same antigen of interest by individually selecting and separating the cells and using each cell to the method for producing an antibody or a fragment of the antibody with specificity toward the antigen of interest described hereinbelow.

<Elimination of Nonspecific Cells During Isolation (Optional)>

The cells isolated in the step (4) are highly possible to show reactivity with the labelled antigen of interest, and thus highly possible to be antibody-producing cells. However, there is actually a possibility of contamination of labelled cells due to nonspecific staining (reaction with the labelled antigen of interest). Therefore, non-specifically stained cells may be eliminated (excluded) by using a labelled antigen of no interest, if necessary. For example, in Example 2, an antigen of no interest, the DsRed protein, is added to a cell staining solution in order to exclude DsRed protein positive cells as non-specifically stained cells. In Example 3, a non-phosphorylated peptide is added to a cell staining solution in order to separate phosphorylated peptide positive cells from non-phosphorylated peptide positive cells.

It is preferable to carry out at least one of steps (1) to (4) above in the presence of an RNase inhibitor from the viewpoint of suppressing degradation of mRNA collected from cells to facilitate preparation of cDNA of a monoclonal antibody with specificity toward an antigen of interest or a fragment thereof. Examples of the RNase inhibitor include DEPC (diethylpyrocarbonate), vanadyl ribonucleotide, inhibitory proteins for ribonuclease A, ribonuclease B and ribonuclease C and anti-ribonuclease antibodies. Examples of commercially available RNase inhibitors include RNase-OUT (Life Technologies Corporation), RNasin® (Promega Corporation), Ribonuclease Inhibitor (derived from pig liver) (Takara Bio Inc.) and the like. It is preferable to carry out all of the steps (1) to (4) in the presence of an RNase inhibitor, and more specifically, it is preferable to add an appropriate amount of RNase inhibitor to solutions containing cells, antibodies and the antigen used in the steps. An appropriate amount of the RNase inhibitor may be appropriately selected according to the type of the RNase inhibitor, the type of the solution and the like.

When materials of the labelled antigen of interest used in the step (3) are prevented from contamination of RNase, the recovery rate of mRNA may be increased and the antibody with specificity toward the antigen of interest may be prepared with an increased efficiency.

<Method for Producing a Monoclonal Antibody with Specificity Toward an Antigen of Interest>

The method for producing a monoclonal antibody with specificity toward an antigen of interest of the present invention includes preparing a monoclonal antibody with specificity toward an antigen of interest from at least one single cell obtained by the cell separation method of the present invention through following steps (5) and (6):

(5) preparing a cDNA by separating mRNA from the at least one cell obtained by the cell separation method of the present invention (a cDNA preparing step); and (6) preparing the antigen specific monoclonal antibody or a fragment thereof from the cDNA obtained in the cDNA preparing step.

According to the method, an antibody which exhibits a specific binding ability to an antigen of interest or an antibody fragment (the fragment per se exhibits a specific binding ability to an antigen of interest) which exhibits a specific binding ability to an antigen of interest may be produced.

(5) cDNA Preparing Step

In the step (5), mRNA is separated from at least one single cell obtained by the cell separation method of the present invention and cDNA is prepared from the separated mRNA.

For separation of mRNA, mRNA in the cells fixed in the step (1) may be defixed (decrosslinked). A manner of defixing may be appropriately selected according to the type of the reversible crosslinking reagent used in the step (1). When the reversible crosslinking reagent used in the step (1) is formalin, defixing may be carried out by heating the isolated cells and when an amino group-containing group coexists during heating, defixing (decrosslinking) may be facilitated. Examples of the amino group-containing group include tris (hydroxymethyl) aminomethane, amino acids, ethanolamine and the like. Defixing allows recovery of mRNA from cells with an increased efficiency and an increase in the recovery of cDNA. The conditions for the heating treatment may be appropriately selected by taking the extent of fixation, the type and concentration of the amino group-containing compound and the stability of mRNA into account. For example, heating may be carried out at 20° C. to 70° C. for 1 to 120 minutes. It is more preferable to carryout defixing by heat treating the isolated cells in the presence of a protease. The conditions for the heating treatment and the amount of the protease may be appropriately selected by taking the type and the amount of the protease, the extent of fixation and the stability of mRNA into account. For example, heating may be carried out at 40° C. to 60° C. for 1 to 120 minutes. The amount of the protease may be in the range of 0.1 μg/ml to 100 μg/ml. The protease may be any existing protease and may be, for example, protease K. The heating treatment in the presence of protease K allows defixing of mRNA from the isolated cells with an increased efficiency and increases the proportion of obtaining variable region gene fragments of antibody genes. As a result, the antigen specific monoclonal antibody may be efficiently prepared in the later step.

When the reversible crosslinking reagent used in the step (1) is dithiobis(succinimidyl propionate) (DSP), defixing may be carried out by treating the isolated cells with a reducing agent such as β-mercaptoethanol and sodium borohydride. Similarly in this case, defixing allows recovery of mRNA in the cells with an increased efficiency and may increase the recovery of cDNA. The conditions for the reducing treatment may be appropriately selected by taking the extent of fixing, the type and concentration of the reducing agent and the stability of mRNA into account. The reducing treatment may be carried out, for example, at 20° C. to 70° C. for 1 to 120 minutes. Defixing by reducing treatment may also be carried out in combination with the protease treatment.

Separation of mRNA from at least one single cell and preparation of cDNA may be carried out according to well-known methods. For example, methods disclosed in PTL 2 and NPL 4 (the method by Kurosawa et al.) may be used (the entire disclosures of PTL 2 and NPL 4 are specifically incorporated herein by reference). It is preferable to separate mRNA from one separated antibody-producing cell in view of obtaining a heavy chain gene and a light chain gene of the antibody toward the antigen of interest. However, mRNA may be separated from two or more separated antibody-producing cells and in this case, the separated mRNA is a mixture of mRNAs from respective cells. For example, when mRNA is separated from two antibody-producing cells, two pairs of heavy chain genes and light chain genes are cloned. In this case, the possibility of obtaining the combination of the correct heavy chain gene and light chain gene is 50%: however, the correct pair may be attained from a technological standpoint. However, the possibility of obtaining the correct combination of the heavy chain gene and the light chain gene from mRNA collected from more than 10 antibody-producing cells is less than 1%. Although it is possible to attain the correct combination, the efficiency decreases. Therefore, mRNA is preferably separated from 10 or less separated antibody-producing cells.

More specifically, collection of mRNA from antibodies toward an antigen of interest and preparation of cDNA from the collected mRNA may be carried out by employing the method disclosed in, for example, WO 2009/091048 (US 2011/0020879 A1) (the entire disclosures of which are specifically incorporated herein by reference). The prepared cDNA may be cloned, if necessary. Cloning may be carried out according to the cloning method employing the homologous recombination disclosed in WO 2009/110606 and US 2011/0117609 A1 (the entire disclosures of which are specifically incorporated herein by reference). Further, the base sequence of the prepared cDNA may be identified. The identification of the base sequence of the cDNA may be carried out by using well-known DNA sequencing methods. By identifying the base sequence of the cDNA, an antibody gene toward the antigen of interest may be identified.

However, in the method of the present invention, it is preferable that the second primer used for cDNA synthesis is modified from the above well-known methods. In the method of the present invention, mRNA is inevitably degraded during the steps before cDNA synthesis. Therefore, the efficacy of full-length cDNA synthesis is low and a smearing band tends to be amplified after normal 5' RACE PCR (compare the bands in "10 min" and the bands in "unfixed" in FIG. 1D which is the results of Example 1. The bands amplified from the cells of "10 min" are smeared. Similar tendency is observed in FIG. 2C which is the results of Example 2).

Thus, in the present invention, it is preferable that the second primer for cDNA synthesis, i.e., a sense primer for the second round of PCR, has the sequence around the initiation codon of an immunoglobulin of interest in order to amplify only the full-length antibody gene. For example, in Example 3 (C), a sequence around the initiation codon of the guinea pig immunoglobulin is used as a sense primer for the second round of PCR. When the sequence around the initiation codon of the immunoglobulin is known, the primer may be prepared based on known information or sequence information of the immunoglobulin gene expressed in the immunized animal (in case of Example 3, guinea pig) obtained by high throughput sequencing.

(6) Antigen Specific Monoclonal Antibody Preparing Step

In the step (6), an antigen specific monoclonal antibody or a fragment thereof is prepared from cDNA prepared in the cDNA preparing step. Preparation of the antigen specific monoclonal antibody or a fragment thereof from cDNA may be carried out according to well-known methods. For example, preparation may be carried out with a fragment of an antibody gene prepared by the method for specifically preparing a DNA fragment disclosed in WO 2011/027808

(the entire disclosure of which is specifically incorporated herein by reference). Disclosures in PTL 2 and NPL 4 (the method by Kurosawa et al.) may also be referred to for preparation of an antibody or a fragment of the antibody. The antibody obtained by the method of the present invention exhibits a specific binding ability to the antigen of interest and the fragment thereof is an antigen-binding fragment which exhibits a specific binding ability to the antigen of interest. Examples of the antigen specific antibody fragment includes Fab, F(ab')2, Fab', diabody, a single stranded antibody (such as scFv and dsFv) and the like. The antibody fragment may be appropriately prepared by utilizing the well-known method after determining the amino acid sequence and base sequence of the antibody gene from cDNA cloned in the step (5).

It is preferable to carry out the step (5) in the presence of an RNase inhibitor from the viewpoint of suppressing degradation of mRNA collected from cells to facilitate preparation of cDNA of a desired antigen specific monoclonal antibody or a fragment thereof. Examples of the RNase inhibitors are those mentioned for the steps (1) to (4). It is preferable to add an appropriate amount of the RNase inhibitor to the solutions used in the step (5) in order to carry out the step in the presence of the RNase inhibitor. An appropriate amount of the RNase inhibitor may be appropriately selected according to the type of the RNase inhibitor, the type of the solution and the like.

In addition to carrying out at least some or all of the steps (1) to (5) of the present invention in the presence of the RNase inhibitor or instead of using the RNase inhibitor, the steps may be carried out under RNase activity suppressing conditions. By carrying out the steps under such conditions, the recovery rate of mRNA may be increased and an antibody with specificity toward the antigen of interest may be prepared with an increased efficiency.

RNase activity may be suppressed by carrying out the experimental procedures under, for example, cooling conditions such as in or on ice.

<Monoclonal Antibody with Specificity Toward an Antigen of Interest>

The present invention encompasses a monoclonal antibody specific to threonine 18-phosphorylated p53 (pT18-p53). The monoclonal antibody encompasses a monoclonal antibody specific to threonine 18-phosphorylated p53 (pT18-p53) having a γ chain comprising a variable region having an amino acid sequence shown in SEQ ID NO: 9 or a κ chain comprising a variable region having an amino acid sequence shown in SEQ ID NO: 10 and a monoclonal antibody specific to threonine 18-phosphorylated p53 (pT18-p53) having a γ chain comprising CDR1, CDR2 and CDR3 having amino acid sequences shown in SEQ ID NOs: 3 to 5, respectively, and a κ chain comprising CDR1, CDR2 and CDR3 having amino acid sequences shown in SEQ ID NOs: 6 to 8, respectively. Any of the antibodies may be prepared by the method of the present invention and the antibody is specifically described in Example 3.

The present invention further encompasses a monoclonal antibody specific to threonine 68-phosphorylated CHK2 (pT68-CHK2). The monoclonal antibody encompasses a monoclonal antibody specific to threonine 68-phosphorylated CHK2 (pT68-CHK2) having a γ chain comprising a variable region having an amino acid sequence shown in SEQ ID NO: 17 or a κ chain comprising a variable region having an amino acid sequence shown in SEQ ID NO: 18 and a monoclonal antibody specific to threonine 68-phosphorylated CHK2 (pT68-CHK2) having a γ chain comprising CDR1, CDR2 and CDR3 having amino acid sequences shown in SEQ ID NOs: 11 to 13, respectively, and a κ chain comprising CDR1, CDR2 and CDR3 having amino acid sequences shown in SEQ ID NOs: 14 to 16, respectively. Any of the antibodies may be prepared by the method of the present invention and the antibody is specifically described in Example 4.

EXAMPLES

The present invention is further specifically described on the basis of Examples which exemplify the present invention. It is not intended that Examples limit the present invention.

Example 1

(A) OKT10 hybridoma cells attached on glass slides were fixed with 2% paraformaldehyde (PFA), 2% glutaraldehyde (GA), acetone, ethanol or 95% ethanol-5% acetic acid at room temperature for 10 minutes (fixing).

The cells were washed with PBS containing 0.1% Triton X-100 (hereinafter PBS containing 0.1% Triton X-100 is referred to as PBST) (cell membrane lysis).

Thereafter, staining was carried out with a Dylight 594-labelled anti-mouse IgG antibody and Dylight 488-labelled CD38 (reaction with a labelled antigen of interest).

For the cells fixed with paraformaldehyde, binding of the antigen, CD38, to antibodies in the cells was observed. For the cells treated with other fixing solutions, binding to CD38 was not observed. The results are shown in FIG. 1A.

(B) OKT10 hybridoma cells were fixed with 2% paraformaldehyde at 4° C. for 20 minutes (fixing).

The cells were then subjected to cell membrane lysis and staining of antibodies in the cells by using 250 µl of PBST containing a Dylight 594-labelled anti-mouse IgG antibody and 5 µl of RNaseOUT—RNase inhibitor (cell membrane lysis and reaction with a labelled antigen of interest).

The cells were recovered by centrifugation (cell isolation).

Thereafter, a cell lysis solution (100 mM Tris HCl (pH 7.5), 500 mM LiCl, 1% lithium dodecylsulphate and 5 mM dithiothreitol) was added to attain a concentration of 40 cells/1 µl. Extraction of mRNA from the cells and cDNA synthesis were carried out according to the method by Kurosawa et al. (Rapid production of antigen-specific monoclonal antibodies from a variety of animals, BMC Biology, 2012, 10:80) (cDNA synthesis).

Briefly, 2.5 µl of the cell lysis solution (100 cells) was added to 3 µg of magnetic beads (Dynabeads) bound to oligo dT25 to allow binding of mRNA in the cells to the magnetic beads. The magnetic beads were then washed once with 3 µl of mRNA washing solution A (10 mM Tris HCl (pH 7.5), 0.15 M LiCl, 0.1% LiDS or 50 mM Tris HCl (pH 8.3)) and then 3 µl of mRNA washing solution B (75 mM KCl, 3 mM $MgCl_2$, 0.1% Triton X, 0.5 mM dNTP, 5 mM DTT and 2 units RNase inhibitor/µL) followed by cDNA synthesis. Briefly, a cDNA synthesis solution (50 mM Tris HCl (pH8.3), 75 mM KCl, 3 mM $MgCl_2$, 0.1% Triton X-100, 0.5 mM dNTP, 5 mM DTT, 2 units RNase inhibitor/µL and 10 units SuperScript III Reverse transcriptase (Invitrogen)) was added to the washed magnetic beads and allowed to react at 40° C. for 1 hour. The magnetic beads were washed with 3 µl of TE solution (10 mM Tris HCl (pH7.5), 1 mM EDTA and 0.1% Triton X) followed by amplification of the mouse immunoglobulin γ chain constant region gene. To the magnetic beads was added 25 µl of PCR reaction solution (10 pmol of the primers 1 and 2, respectively, 10 nmol of dNTP and 1U of Takara Bio PrimeSTAR heat resistant DNA polymerase) and the reaction was carried out for 35 cycles of 94° C. for 30 seconds and 68° C. for 40 seconds. The primers used were

```
                                            (SEQ ID NO: 1)
5'-GTGGAACTCAGGCGCCCTGACCAGC-3'
and (SEQ ID NO: 2)
5'-ACGCTGCTGAGGGAGTAGAGTCCTGAG-3'.
```

Figure 1B:
FIG. 1B shows an electrophoretic image of Example 1 (B).

Amplification of the immunoglobulin heavy chain constant region gene fragment was observed for the cells fixed with paraformaldehyde. The results are shown in FIG. 1B.
(C) Hybridoma cells ($1×10^6$ cells) were fixed with 2% paraformaldehyde at 4° C. for 10 minutes to 30 minutes (fixing).

The cells were collected by centrifugation to which 250 μL of PBST containing a Dylight 488-labelled anti-mouse IgG antibody and 200 units of RNaseOUT was added to allow antigen-antibody reaction at 4° C. for 15 minutes (cell membrane lysis and reaction with a labelled antigen of interest).

Figure 1C:
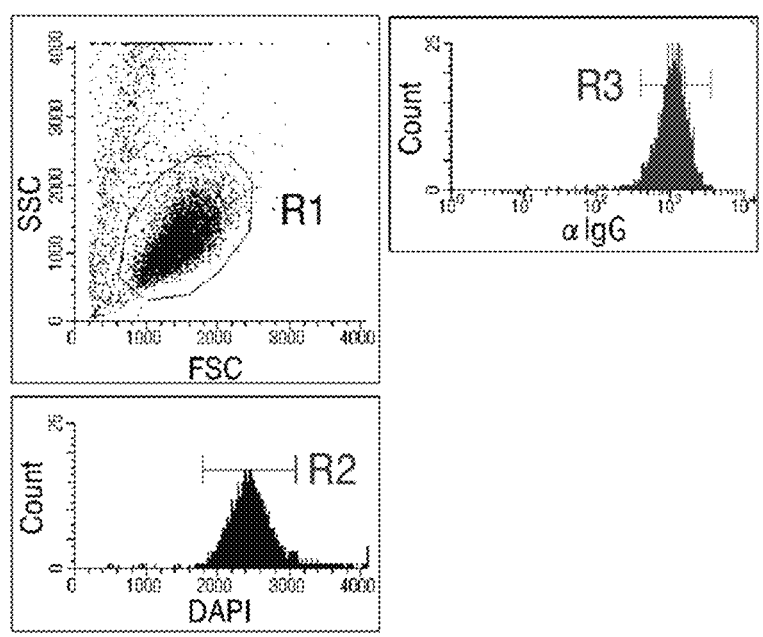
FIG. 1C shows FACS results in Example 1 (C).
Figure 1D:
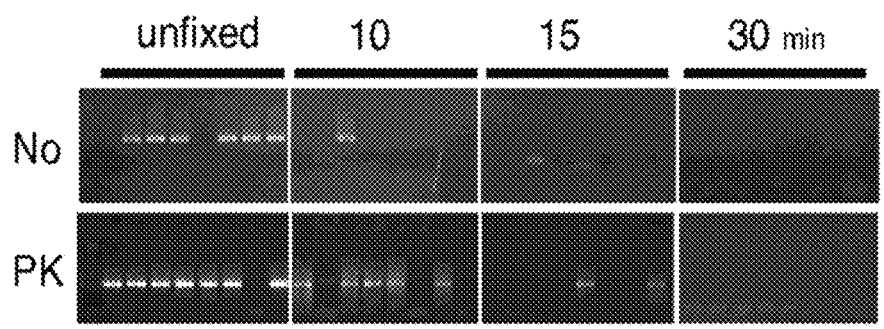
FIG. 1D shows electrophoretic images of Example 1 (D).
Figure 1E:
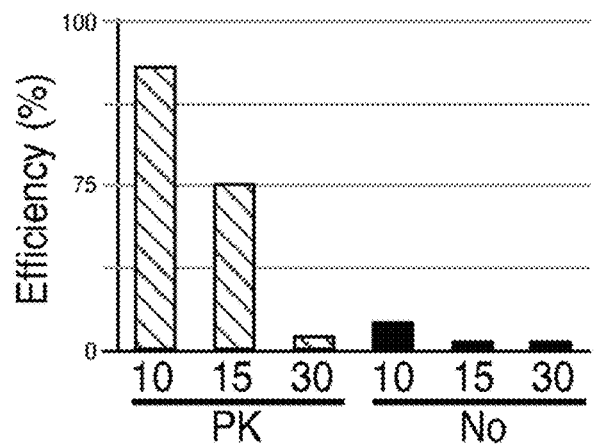
FIG. 1E shows the amplification success rate in Example 1 (E).

The labelled anti-mouse IgG antibody used was diluted in PBST containing RNaseOUT and left to stand at room temperature for 1 hour before use. The cells were diluted in 3 ml of PBS containing 0.1 μg/mL DAPI (4', 6-diamidino-2-phenylindole) and subjected to FACS. The cells were R1 and R2 gated to select single cells. The cells were R3 gated to select the cells having the intracellular immunoglobulin bound to the labelled antibody (cell isolation). The results are shown in FIG. 1C.
(D) The R3-gated cells obtained in the above (C) were subjected to single sorting in 15 μl of cell lysis solution containing 3 μg of magnetic beads or in 15 μl of cell lysis solution containing 3 μg of magnetic beads containing 1 μg/mL of protease κ. The cell lysis solution containing protease κ was further heated at 50° C. for 1 hour in order to decrosslink the linkages formed by paraformaldehyde. Amplification of the full-length immunoglobulin variable region from the cells was carried out according to the method by Kurosawa et al. (NPL 4). It was found that decrosslinking the cells undergone fixing over a short period of time allowed efficient amplification of the full-length immunoglobulin variable region from a single hybridoma cell. The results are shown in FIG. 1D.
(E) The results in (D) are summarized in a graph. The experiments were repeated three times and the averages and the sample standard deviations are shown (N=12). The results are shown in FIG. 1E.

Example 2

OKT10 hybridoma cells and Jurkat cells were mixed at ratios of 1:100 (1%), 1:1000 (0.1%), 1:10,000 (0.01%) and 1:100,000 (0.001%). The cells were fixed with a 2% paraformaldehyde PBS solution at 4° C. for 10 minutes (fixing).

The cells were collected by centrifugation to which 250 μl of staining solution (PEST containing anti-mouse IgG Dylight 488, anti-mouse IgG Dylight 650, 0.1 μg/ml of DsRed and 200 units of RNaseOUT) was added and left on ice for 15 minutes (cell membrane lysis and reaction with a labelled antigen of interest).

Figure 2A:
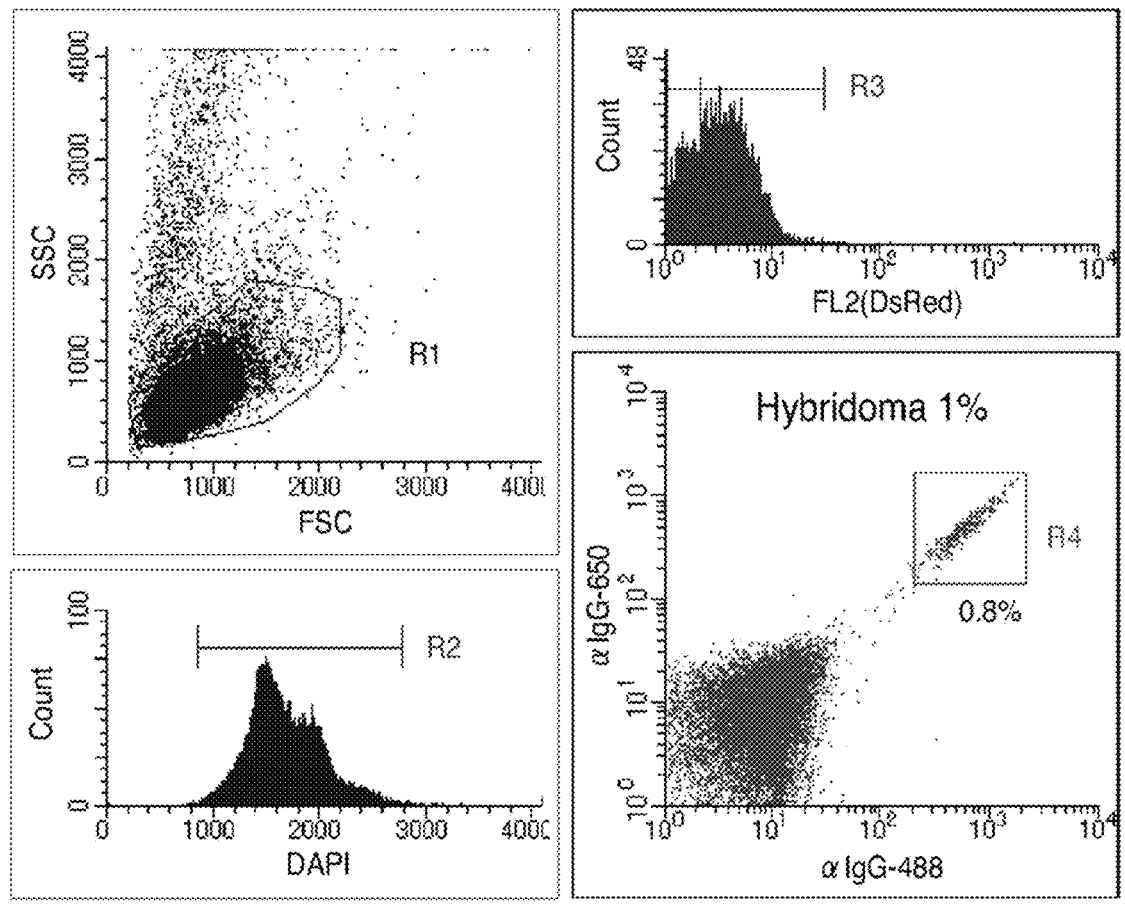
FIG. 2A shows FACS results in Example 2 (A).
Figure 2B:
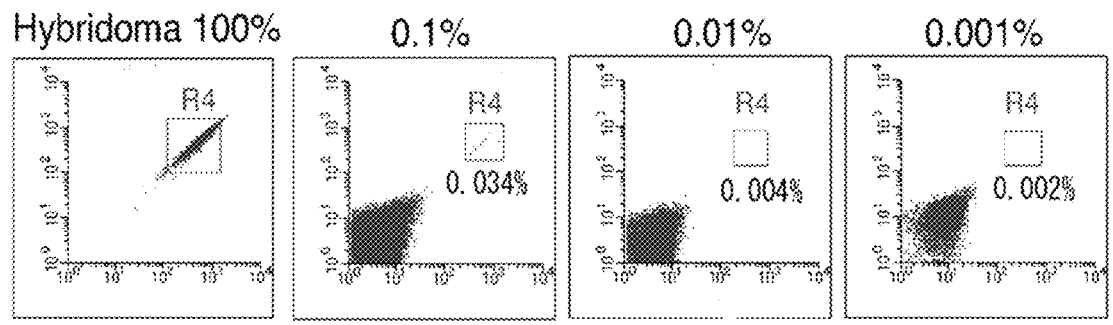
FIG. 2B shows FACS results in Example 2 (B).
Figure 2C:
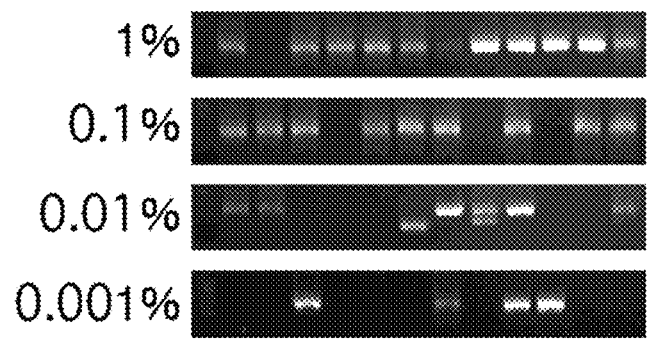
FIG. 2C shows electrophoretic images of Example 2 (C).
Figure 2D:
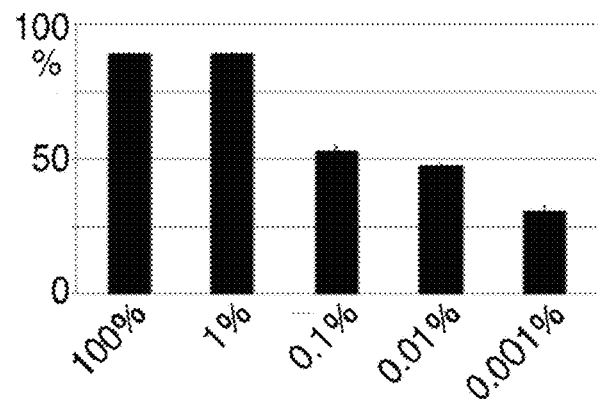
FIG. 2D shows the amplification success rates in Example 2 (D).

To the solution was added 3 ml of PBS solution containing 1 μg/ml of DAPI and OKT10 hybridoma cells were isolated with a flow cytometer. The cells were R1 (FSC vs SSC) and R2 (DAPI) gated to identify a single cell population. From the single cell population, cells having autofluorescence and non-specifically stained cells were eliminated with the FL2 channel (R3 gate). From the cells, anti-mouse IgG Dylight 488 strongly positive and anti-mouse IgG Dylight 650 strongly positive cells were identified as OKT10 hybridoma cells (R4) (cell isolation).
(A) FIG. 2A is a FACS graph of OKT10 hybridoma cells and Jurkat cells mixed at 1:100 (1%).
(B) FIG. 2B is a FACS graph for the mixing ratios of 100%, 0.1%, 0.01% and 0.001%. In all cases, cells were observed in the R4 gate corresponding to the hybridoma cells.
(C) The R4-gated cells were subjected to single cell sorting in 15 μL of cell lysis solution containing 3 μg of oligo-dT magnetic beads and 1 μg/ml of protease κ. According to the method described in Example 1 (B), RNA extraction from the cells, cDNA synthesis and V gene amplification by 5' RACE PCR were carried out. The results are shown in FIGS. 2C and 2D. When the V gene was amplified from the cell lysis solution of 72 cells, the amplification success rates were 89%, 53%, 47% and 31% for mixing ratios of 1%, 0.1%, 0.01% and 0.001%, respectively.

Example 3

(A) The iliac lymph node was collected from a guinea pig immunized with p53 phosphorylated peptide and a cell suspension was prepared therefrom. Cells ($1×10^7$ cells) were fixed with 2% paraformaldehyde PBS solution at 4° C. for 10 minutes (fixing).

The cells were collected by centrifugation to which 250 μl of staining solution (PBST containing anti-guinea pig IgG Dylight 650, phosphorylated peptide-streptavidin Dylight 488, non-phosphorylated peptide-streptavidin Dylight 550, 0.1 μg/ml of DsRed and 200 units of RNaseOUT) was added and left on ice for 15 minutes for staining (cell membrane lysis and reaction with a labelled antigen of interest).

Figure 3A:
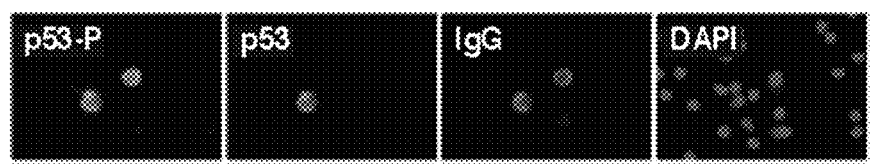
FIG. 3A shows fluorescence micrographs of Example 3 (A).

To the solution was added 3 ml of PBS solution containing 1 μg/ml of DAPI and a partial sample was observed under a fluorescence microscope. The results are shown in FIG. 3A.

As a result, the phosphorylated p53 specific plasma cells were identified as anti-guinea pig IgG strongly positive, phosphorylated peptide-streptavidin strongly positive and non-phosphorylated peptide-streptavidin negative.

The p53 specific plasma cells were identified as anti-guinea pig IgG strongly positive, phosphorylated peptide-streptavidin strongly positive and non-phosphorylated peptide-streptavidin strongly positive.

Figure 3B:
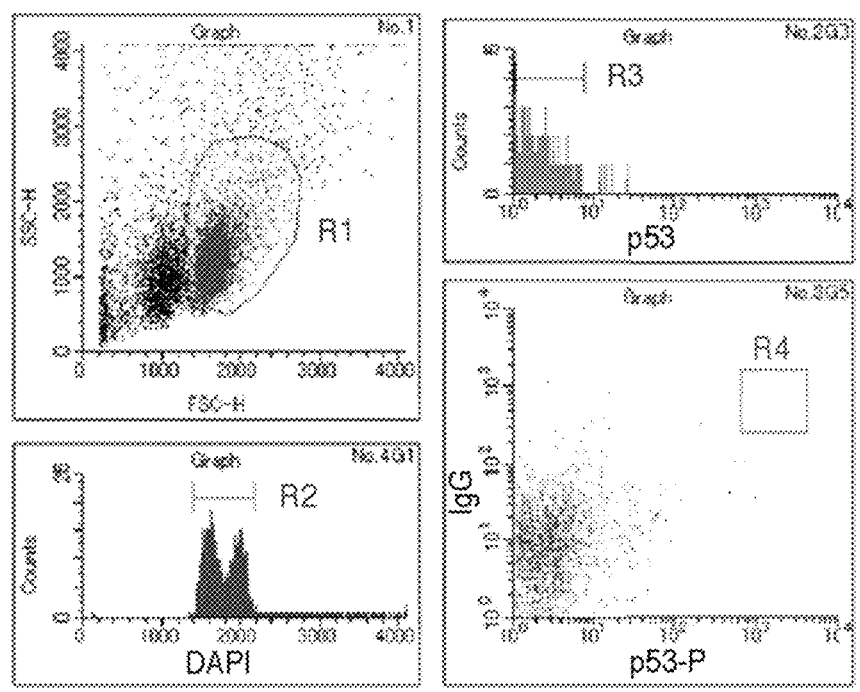
FIG. 3B shows FACS results in Example 3 (B).

Non-specific plasma cells were identified as anti-guinea pig IgG strongly positive, phosphorylated peptide-streptavidin negative and non-phosphorylated peptide-streptavidin negative.
(B) The cells were analyzed on a flow cytometer in order to separate the p53 specific plasma cells. The cells were R1 (FSC vs SSC) and R2 (DAPI) gated to identify a single cell population. From the single cell population, cells having autofluorescence, non-specifically stained cells and p53 specific plasma cells reacting with the non-phosphorylated peptide were eliminated with the FL2 channel (R3 gate). From the cells, anti-mouse IgG strongly positive and phosphorylated peptide strongly positive cells were identified as the phosphorylated p53 specific plasma cells (R4). The cells appearing in the R4 gate had 100 times and 10 times stronger fluorescence intensities than other cells with regard to the binding to the phosphorylated peptide and to the anti-guinea pig antibody, respectively. The results are shown in FIG. 3B.

Figure 3C:
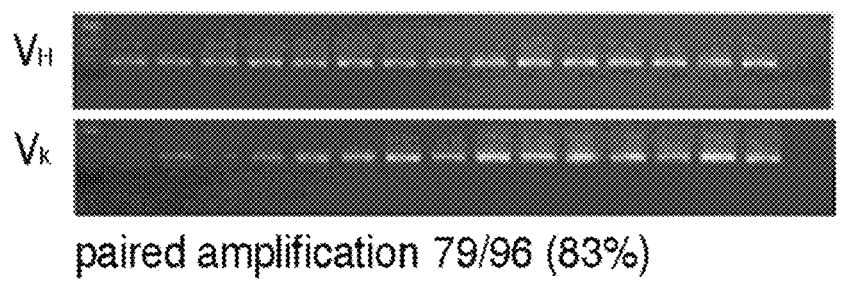
FIG. 3C shows electrophoretic images of Example 3 (C).

(C) The R4-gated cells were subjected to single cell sorting by the same manner as in Example 2 (cell isolation). Thereafter, the V gene was amplified by 5' RACE PCR by the same manner as in Example 1 (B). The results are shown in FIG. 3C. When the V gene was amplified from the cell lysis solution of 72 cells, the amplification efficiency was 84%.

Figures 3D, 3E:
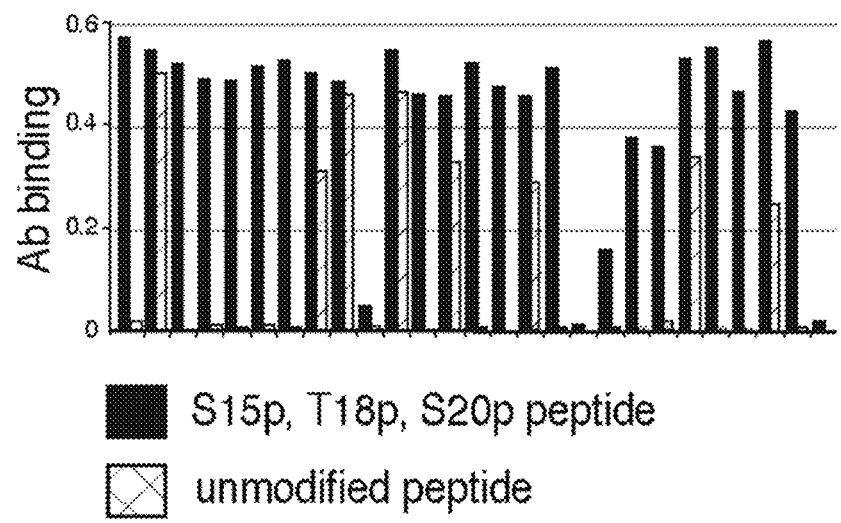
FIG. 3D shows results of specificity analysis by ELISA in Example 3 (D).
FIG. 3E shows FACS results in Comparative Example 1 (A).

(D) From the obtained V gene, the full-length heavy chain and light chain immunoglobulin genes were prepared according to the method by Kurosawa et al. (NPL 4) which were introduced into 293FT cells to prepare recombinant antibodies. The obtained antibodies were analyzed for the specificity by ELISA. The results are shown in FIG. 3D. 93% (25/27) bound to the phosphorylated peptide, among which 68% (17/25) were specific to the phosphorylated peptide.

Comparative Example 1 (method in NPL 4)

(A) From the iliac lymph node of a guinea pig immunized with the p53 phosphorylated peptide, a cell suspension was prepared. The cells (1×10⁷ cells) were suspended in PBS containing anti-guinea pig IgG Dylight 650, phosphorylated peptide-streptavidin Dylight 488, non-phosphorylated peptide-streptavidin Dylight 550 and ER-tracker and left to stand at 4° C. for 30 minutes to stain the cells.

The cells were analyzed on a flow cytometer in order to separate the p53 specific plasma cells. The cells were R1 (FSC vs SSC) gated to identify a single cell population. From the single cell population, cells having autofluorescence, non-specifically stained cells and p53 specific plasma cells reacting with the non-phosphorylated peptide were eliminated with the FL2 channel (R2 gate). The ER-tracker strongly positive cells were selected to identify plasma cells (R3 gate) from which anti-guinea pig IgG weakly positive and phosphorylated peptide positive cells were identified as phosphorylated p53 specific plasma cells (R4). The cells appearing in the R4 gate had only 10 times and a few times stronger fluorescence intensities than other cells with regard to the binding to the phosphorylated peptide and to the anti-guinea pig antibody, respectively. The results are shown in FIG. 3E.

Figure 3F:
FIG. 3F shows electrophoretic images of Comparative Example 1 (B).

(B) The R4-gated cells were subjected to single cell sorting by the same manner as in Example 2 (cell isolation). Thereafter, the V gene was amplified by 5' RACE PCR by the same manner as in Example 1 (B). The results are shown in FIG. 3F. When the V gene was amplified from the cell lysis solution of 72 cells, the amplification efficiency was 16%.

Figure 3G:
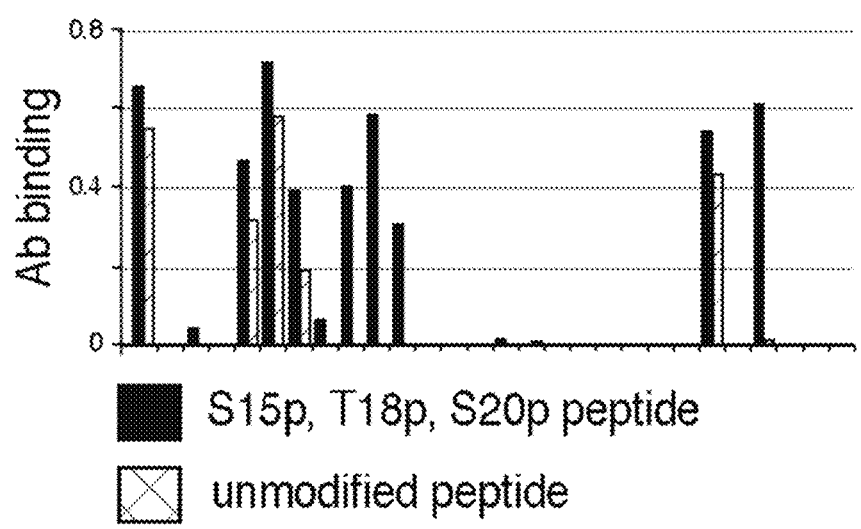
FIG. 3G shows results of specificity analysis by ELISA in Comparative Example 1 (C).

(C) From the obtained V gene, the full-length heavy chain and light chain immunoglobulin genes were prepared by the same manner as in Example 3 (D) which were introduced into 293FT cells to prepare recombinant antibodies. The obtained antibodies were analyzed for the specificity by ELISA. As a result (see FIG. 3G), 33% (9/27) bound to the phosphorylated peptide among which 44% (4/9) were specific to the phosphorylated peptide.

The results in Example 3 and Comparative Example 1 are summarized in Table 1 below. The significant effect of the present invention is apparent.

TABLE 1

|  | V gene amplification efficiency | Number of antibodies bound to phosphorylated peptide | Number of antibodies specific to phosphorylated peptide |
| --- | --- | --- | --- |
| Example 3 | 84% | 93% (25/27) | 63% (17/27) |
| Comparative Example 1 | 16% | 33% (9/27) | 15% (4/27) |

Example 3 (Continued)

Figure 3H:
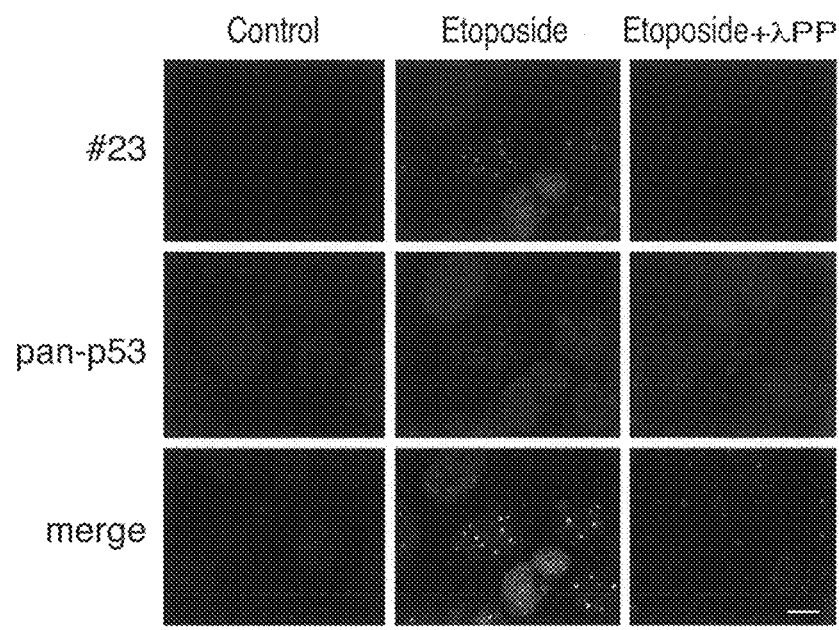
FIG. 3H shows fluorescence micrographs after immunostaining in Example 3 (E).
Figure 3I:
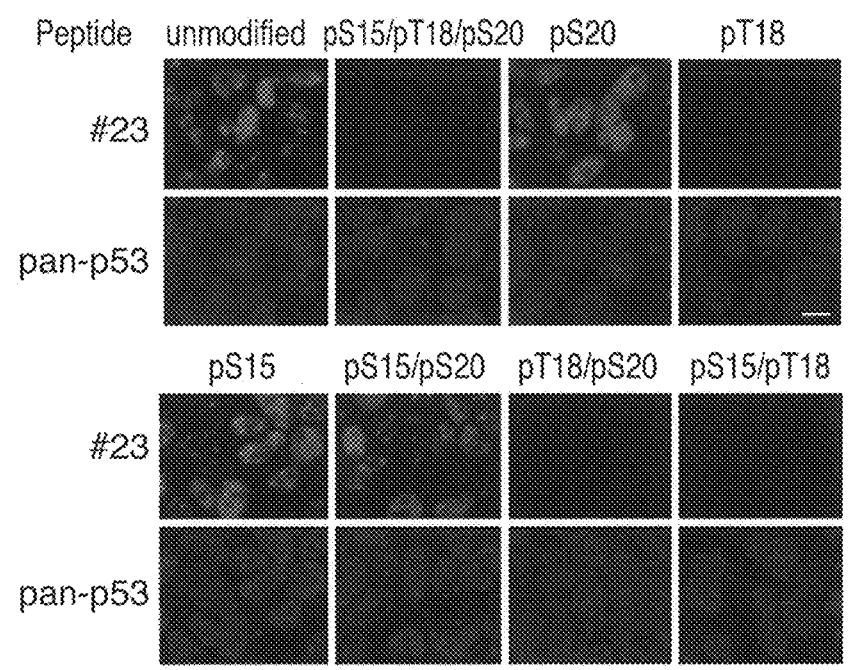
FIG. 3I shows fluorescence micrographs after immunostaining in Example 3 (E).
Figure 3J:
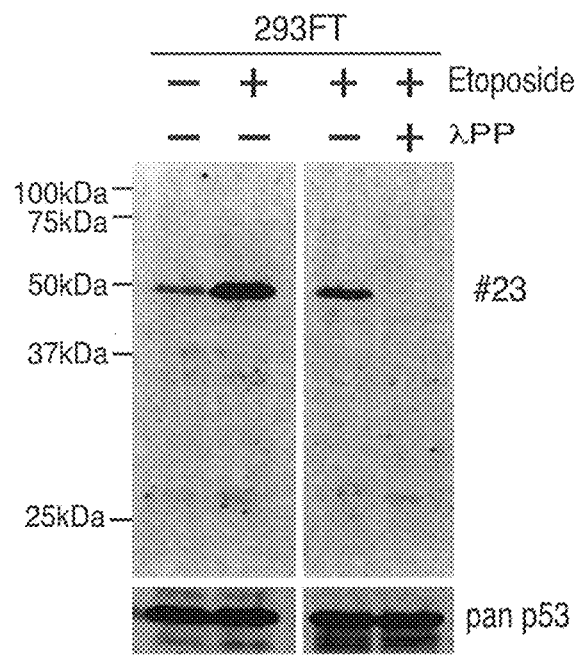
FIG. 3J shows results of western blotting in Example 3 (E).
Figure 3K:
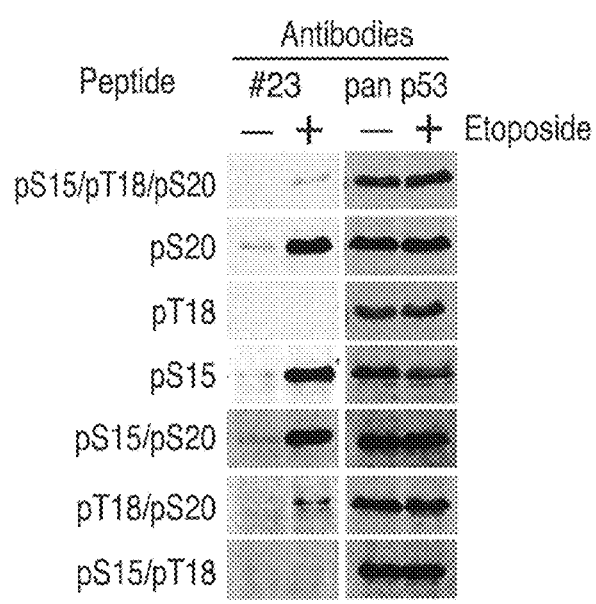
FIG. 3K shows results of western blotting in Example 3 (E).

(E) In order to prepare a monoclonal antibody specific to threonine 18-phosphorylated p53 (pT18-p53), HEK293 cells were subjected to immunostaining with antibody clones obtained in Example 3 (D). The #23 antibody was identified as an antibody clone which allowed specific signal detection in the nuclei of HEK293 cells in which DNA damage was caused by etoposide treatment. The signal obtained with the #23 antibody disappeared in the cells treated with λ phosphatase. The results are shown in FIG. 3H. The signal also disappeared in the presence of the p53 peptide having pT18, while the signal did not disappear in the presence of the peptides in which neighboring serine 15 and serine 20 were phosphorylated. The results are shown in FIG. 3I. In western blotting analysis, the #23 antibody allowed detection of a specific band at 50 kDa from the etoposide treated HEK293. The signal obtained with the #23 antibody disappeared in the cells treated with λ phosphatase. The results are shown in FIG. 3J. The signal also disappeared in the presence of excess p53 peptide having pT18, while the signal did not disappear in the presence of the peptides in which neighboring serine 15 and serine 20 were phosphorylated. The results are shown in FIG. 3K.

Figure 3L:
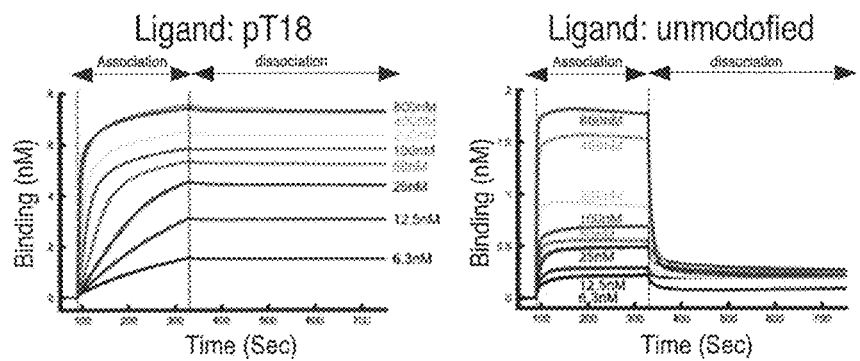
FIG. 3L shows results of surface plasmon resonance (SPR) analysis in Example 3 (F).

(F) The affinity of the #23 antibody toward pT18-p53 was measured on a surface plasmon resonance (SPR) device. As a result, the #23 antibody had a binding constant $K_D$ of 0.20 nM toward the pT18-p53 peptide. The results are shown in FIG. 3L.

(G) The amino acid sequences (SEQ ID NOs: 3 to 5) of CDR1, CDR2 and CDR3 of the γ chain and the amino acid sequences (SEQ ID NOs: 6 to 8) of CDR1, CDR2 and CDR3 of the kappa chain of the #23 antibody are respectively shown in Table 2. The amino acid sequences (SEQ ID NOs: 9 and 10) of the variable regions of the γ and kappa chains of the #23 antibody are respectively shown in Table 3.

TABLE 2

|  | CDR1 | CDR2 | CDR3 |
| --- | --- | --- | --- |
| p53 #23 gamma | GFIFSSYA | ISRSDSNR | SRYRDYY-ALDI |
| p53 #23 kappa | QSLLHSNGKTY | RVS | FQNTHPPLT |

TABLE 3

|  | Full V seq |
| --- | --- |
| p53 #23 gamma | MELALSWVFLFTLLRGVQAEEQLVESGGGLVQPGGSLKLSCLASGFIFSSYAMNWVRQAPGKGLEWISAISRSDSNRYYTDSVKGRFTISRDDGTNTLYLQMSSLRPEDTAVYYCSRYRDYYALDI |

TABLE 3-continued

Full V seq

| | |
|---|---|
| p53 #23 kappa | MRIPVHLLGLLLLWITGSTGDVVMTQTPLSLSVSPGEPASI SCRASQSLLHSNGKTYLHWVVHKPGQAPRGMIFRVSNKYSG TPERFSGSGSGTDFTLKISRVEAEDAGVYYCFQNTHPPLT |

Example 4

(A) In order to prepare a monoclonal antibody specific to threonine 68 phosphorylated CHK2 (pT68-CHK2), the iliac lymph node was collected from a guinea pig immunized with pT68-CHK2 peptide and a cell suspension was prepared therefrom. Cells ($1\times10^7$ cells) were fixed with 2% paraformaldehyde PBS solution at 4° C. for 10 minutes (fixing).

The cells were collected by centrifugation to which 250 μl of staining solution (PBST containing anti-guinea pig IgG Dylight 650, pT68-CHK2 peptide-streptavidin Dylight 488, non-phosphorylated peptide (UM-CHK2)-streptavidin Dylight 550, 0.1 μg/ml of DsRed and 200 units of RNase-OUT) was added and left on ice for 15 minutes for staining (cell membrane lysis and reaction with a labelled antigen of interest).

To the solution was added 3 ml of PBS solution containing 1 μg/ml of DAPI, thereby the cell nucleus was stained.

Figure 4A:
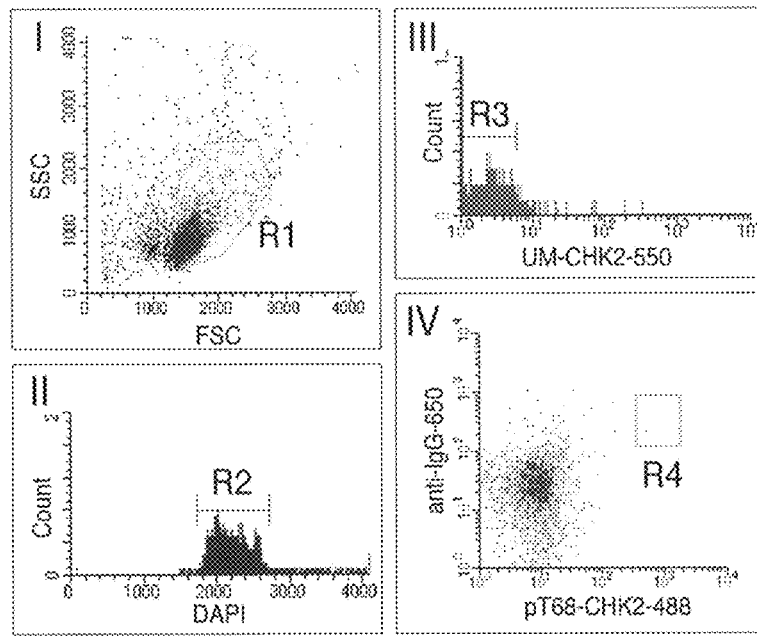
FIG. 4A shows FACS results in Example 4 (A).

(B) The cells were analyzed on a flow cytometer in order to separate pT68-CHK2 specific plasma cells. The cells were R1 (FSC vs SSC) and R2 (DAPI) gated to identify a single cell population. From the single cell population, cells having autofluorescence, non-specifically stained cells and CHK2 specific plasma cells reacting with the UM-CHK2 peptide were eliminated with the FL2 channel (R3 gate) . From the cells, anti-mouse IgG strongly positive and pT68-CHK2 peptide strongly positive cells were identified as pT68-CHK2 specific plasma cells (R4) . The cells appearing in the R4 gate had 100 times and 10 times IgG stronger fluorescence intensities than other cells with regard to the binding to the pT68-CHK2 peptide and to the anti-guinea pig antibody, respectively. The results are shown in FIG. 4A.

Figure 4B:
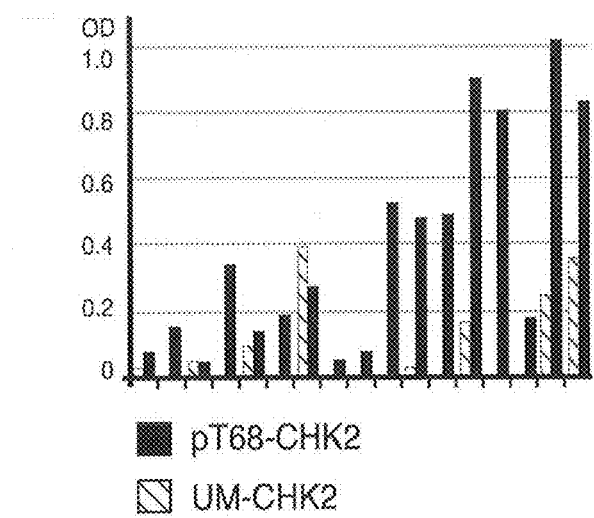
FIG. 4B shows results of specificity analysis by ELISA in Example 4 (B).

(C) The R4-gated cells were subjected to single cell sorting by the same manner as in Example 2 (cell isolation). Thereafter, the V gene was amplified by isolated 5' RACE PCR by the same manner as in Example 1 (B), the full-length heavy chain and light chain immunoglobulin genes were prepared from the obtained V gene according to the method by Kurosawa et al. (NPL 4) and the genes were introduced into 293FT cells to prepare recombinant antibodies. The obtained antibodies were analyzed for the specificity by ELISA. The results are shown in FIG. 4B. Among the antibodies, 59% (10/17) were specific to the pT68-CHK2 peptide.

Figure 4C:
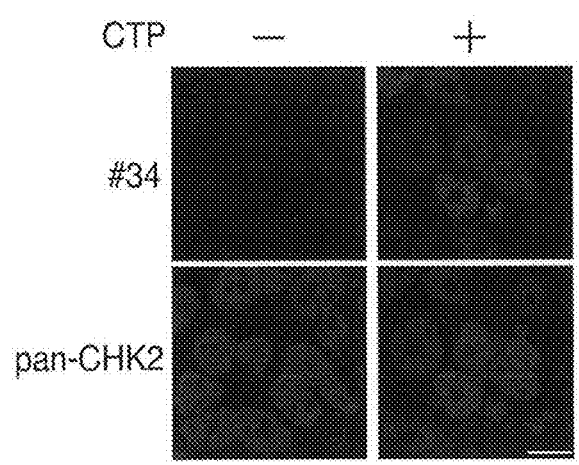
FIG. 4C shows fluorescence micrographs of Example 4 (C).
Figure 4D:
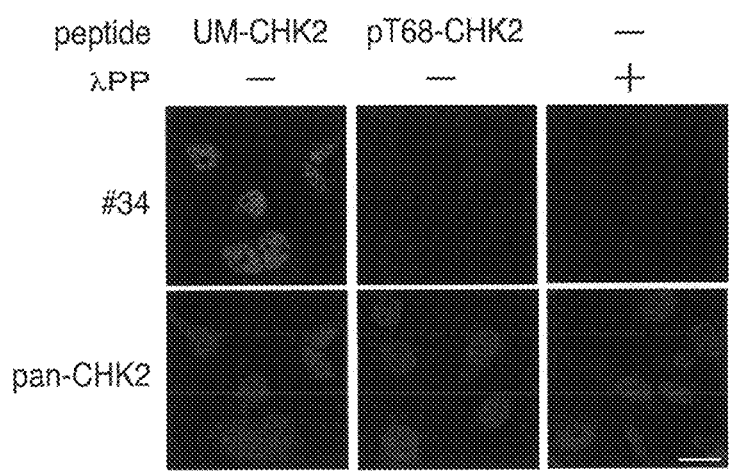
FIG. 4D shows fluorescence micrographs of Example 4 (D).

(D) With the obtained antibody clones, HEK293 cells and Hela cells were immunostained. The #34 antibody was identified as an antibody clone which allowed specific signal detection in the nuclei of HEK293 cells in which DNA break was induced by camptothecin treatment. The results are shown in FIG. 4C. The signal disappeared in the presence of excess pT68-CHK2 peptide, while the signal did not disappear in the presence of the UM-CHK2 peptide. The signal also disappeared in the cells treated with λ phosphatase. The results are shown in FIG. 4D.

From the above results, it was found that the #34 antibody allows detection of endogenous CHK2 in which threonine 68 is phosphorylated.

Figure 4E:
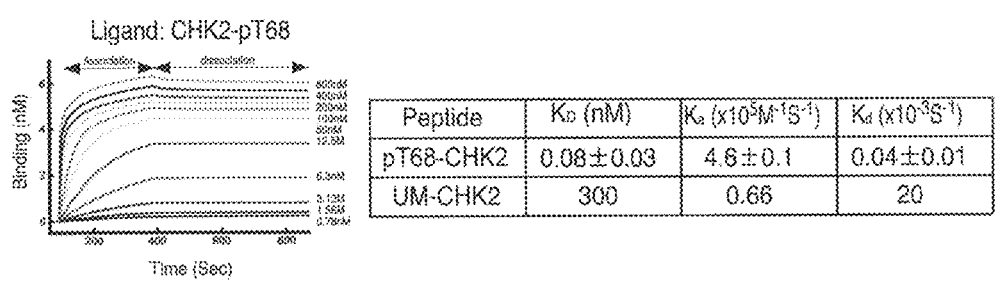
FIG. 4E shows results of surface plasmon resonance (SPR) analysis in Example 4 (E).

(E) The affinity of the #34 antibody toward pT68-CHK2 was measured on a surface plasmon resonance (SPR) device. As a result, the #34 antibody had a binding constant $K_D$ of 0.08 nM toward the pT68-CHK2 peptide. The results are shown in FIG. 4E.

(F) The amino acid sequences (SEQ ID NOs: 11 to 13) of CDR1, CDR2 and CDR3 of the γ chain and the amino acid sequences (SEQ ID NOs: 14 to 16) of CDR1, CDR2 and CDR3 of the kappa chain of the #34 antibody are respectively shown in Table 4 (SEQ ID NO). The amino acid sequences (SEQ ID NOs: 17 and 18) of the variable regions of the γ and kappa chains of the #34 antibody are respectively shown in Table 5.

TABLE 4

| | CDR1 | CDR2 | CDR3 |
|---|---|---|---|
| CHK2 #34 gamma | GFTFSNYF | ISGDSSNI | TRLMVVTHLDI |
| CHK2 #34 kappa | QSLLYSRNNKNL | WAS | WQGISAPNTG |

TABLE 5

Full V seq

| | |
|---|---|
| CHK2 #34 gamma | MELALSWVFLLFILKGVQADVQLVESGGGLVQPGGSLRLSC VASGFTFSNYFMYWVRQAPGKGLEWLAAISGDSSNIKYADS VKGRFTISRDNSKNTLYLQMSSLRTEDTAVYYCTRLMVVTH LDI |
| CHK2 #34 kappa | MLLTVLLWVSGVCGDIVMTQSPVSLIVSPGESATIRCQSSQ SLLYSRNNKNLLNWYQQKPGQSPKLLIYWASTRTSGIPERF SGSGSGTAFTLTISGAQAEDVATYYCWQGISAPNT |

[Industrial Applicability]

The present invention is useful in the field relating to antibody preparation.

[Sequence Listing Free Text]

SEQ ID NO: 1 PCR primer

SEQ ID NO: 2 PCR primer

SEQ ID NOs: 3 to 5 CDR1, CDR2 and CDR3 of the γ chain of pT18-p53 specific monoclonal antibody SEQ ID NOs: 6 to 8 CDR1, CDR2 and CDR3 of the kappa chain of pT18-p53 specific monoclonal antibody SEQ ID NO: 9 Variable region of the γ chain of pT18-p53 specific monoclonal antibody SEQ ID NO: 10 Variable region of the kappa chain of pT18-p53 specific monoclonal antibody SEQ ID NOs: 11 to 13 CDR1, CDR2 and CDR3 of the γ chain of pT68-CHK2 specific monoclonal antibody SEQ ID NOs: 14 to 16 CDR1, CDR2 and CDR3 of the kappa chain of pT68-CHK2 specific monoclonal antibody SEQ ID NO: 17 Variable region of the γ chain of pT68-CHK2 specific monoclonal antibody SEQ ID NO: 18 Variable region of the κ chain of pT68-CHK2 specific monoclonal antibody

We claim:

1. A method for producing a monoclonal antibody with specificity toward an antigen of interest from at least one isolated cell, wherein the method comprises the following steps;
   (1) a fixing step of fixing a cell population containing antibody-producing cells with a crosslinking reagent, wherein the crosslinking reagent is a reversible crosslinking regent having the cell membrane permeability;
   (2) a cell membrane lysis step of treating the fixed cell population with a detergent;
   (3) a staining step of intracellularly reacting a cell membrane of the lysed cell population with the antigen of interest having a label;
   (4) isolating at least one cell which has been reacted intracellularly with the antigen of interest having the label from the cell population that underwent the staining step, and
   (5) a cDNA preparing step comprising preparing a cDNA by separating mRNA from the at least one isolated cell by a decrosslinking treatment of the at least one isolated cell; and
   (6) preparing the monoclonal antibody or fragment thereof with specificity toward the antigen of interest from the cDNA obtained in the cDNA preparing step, and
   wherein the cell membrane lysis step (2) and the staining step (3) can be carried out sequentially or in parallel.

2. The method according to claim 1, wherein the crosslinking reagent is formalin or a bivalent crosslinking reagent having an S—S bond in a spacer chain.

3. The method according to claim 1, wherein the detergent is at least one detergent selected from the group consisting of a nonionic detergent, an amphoteric detergent and an ionic detergent.

4. The method according to claim 1, wherein the detergent is a nonionic detergent.

5. The method according to claim 1, wherein at least one step of steps (1) to (4) is carried out in a presence of an RNase inhibitor.

6. The method according to claim 1, wherein at least step (5) is carried out in a presence of an RNase inhibitor.

7. The method according to claim 1, wherein the at least one isolated cell in step (5) is 10 or less isolated cells and the mRNA separation is performed on the 10 or less isolated cells.

8. The method according to claims 1, wherein a primer having a sequence corresponding to a region around an initiation codon of an immunoglobulin of interest is used as a sense primer of a second PCR of 5' RACE PCR in the cDNA preparation of step (5).

9. The method according to claim 1, wherein the decrosslinking treatment is a heating treatment if the crosslinking reagent is formalin.

10. The method according to claim 9, wherein the heating treatment is carried out in a presence of a protease to obtain fragments of antibody variable region genes.

11. The method according to claim 1, wherein the decrosslinking treatment is a reduction treatment if the crosslinking reagent is a bivalent crosslinking reagent having an S—S bond in a spacer chain.

12. A monoclonal antibody specific to threonine 18-phosphorylated p53 (pT18-p53) selected from a monoclonal antibody:
   (i) having a gamma chain comprising a variable region having an amino acid sequence of SEQ ID NO: 9 and a kappa chain comprising a variable region having an amino acid sequence of SEQ ID NO: 10, and
   (ii) having a gamma chain comprising CDR1, CDR2 and CDR3 having amino acid sequences of SEQ ID NOs: 3 to 5, respectively, and a kappa chain comprising CDR1, CDR2 and CDR3 having amino acid sequences of SEQ ID NOs: 6 to 8, respectively.

13. The monoclonal antibody as claimed in claim 12, having a gamma chain comprising CDR1, CDR2 and CDR3 having amino acid sequences of SEQ ID NOs: 3 to 5, respectively, and a kappa chain comprising CDR1, CDR2 and CDR3 having amino acid sequences of SEQ ID NOs: 6 to 8, respectively.

14. A monoclonal antibody specific to threonine 68-phosphorylated CHK2 (pT68-CHK2) selected from a monoclonal antibody
   (i) having a gamma chain comprising a variable region having an amino acid sequence of SEQ ID NO: 17 and a kappa chain comprising a variable region having an amino acid sequence of SEQ ID NO: 18, and
   (ii) having a gamma chain comprising CDR1, CDR2 and CDR3 having amino acid sequences of SEQ ID NOs: 11-13, respectively, and a kappa chain comprising CDR1, CDR2 and CDR3 having amino acid sequences of SEQ ID NOs: 14-16, respectively.

15. The monoclonal antibody as claimed in claim 14, having a gamma chain comprising CDR1, CDR2 and CDR3 having amino acid sequences of SEQ ID NOs: 11-13, respectively, and a kappa chain comprising CDR1, CDR2 and CDR3 having amino acid sequences of SEQ ID NOs: 14-16, respectively.

16. The monoclonal antibody as claimed in claim 12 having a gamma chain comprising a variable region having an amino acid sequence of SEQ ID NO: 9 and a kappa chain comprising a variable region having an amino acid sequence of SEQ ID NO: 10.

17. The monoclonal antibody as claimed in claim 15 having a gamma chain comprising a variable region having an amino acid sequence of SEQ ID NO: 17 and a kappa chain comprising a variable region having an amino acid sequence of SEQ ID NO: 18.

* * * * *

SEQUENCE LISTING

<160> NUMBER OF SEQ ID NOS: 18

<210> SEQ ID NO 1
<211> LENGTH: 25
<212> TYPE: DNA
<213> ORGANISM: Artificial sequence
<220> FEATURE:
<223> OTHER INFORMATION: Synthetic primer sequence

<400> SEQUENCE: 1
gtggaactca ggcgccctga ccagc                                   25

<210> SEQ ID NO 2
<211> LENGTH: 27
<212> TYPE: DNA
<213> ORGANISM: Artificial sequence
<220> FEATURE:
<223> OTHER INFORMATION: Synthetic primer sequence

<400> SEQUENCE: 2
acgctgctga gggagtagag tcctgag                                 27

<210> SEQ ID NO 3
<211> LENGTH: 8
<212> TYPE: PRT
<213> ORGANISM: Cavia porcellus

<400> SEQUENCE: 3

Gly Phe Ile Phe Ser Ser Tyr Ala
1               5

<210> SEQ ID NO 4
<211> LENGTH: 8
<212> TYPE: PRT
<213> ORGANISM: Cavia porcellus

<400> SEQUENCE: 4

Ile Ser Arg Ser Asp Ser Asn Arg
1               5

<210> SEQ ID NO 5
<211> LENGTH: 11
<212> TYPE: PRT
<213> ORGANISM: Cavia porcellus

<400> SEQUENCE: 5

Ser Arg Tyr Arg Asp Tyr Tyr Ala Leu Asp Ile
1               5                   10

<210> SEQ ID NO 6
<211> LENGTH: 11
<212> TYPE: PRT
<213> ORGANISM: Cavia porcellus

<400> SEQUENCE: 6

Gln Ser Leu Leu His Ser Asn Gly Lys Thr Tyr
1               5                   10

<210> SEQ ID NO 7
<211> LENGTH: 3
<212> TYPE: PRT
<213> ORGANISM: Cavia porcellus

<400> SEQUENCE: 7

Arg Val Ser

<210> SEQ ID NO 8
<211> LENGTH: 9
<212> TYPE: PRT
<213> ORGANISM: Cavia porcellus

<400> SEQUENCE: 8

Phe Gln Asn Thr His Pro Pro Leu Thr
1               5

<210> SEQ ID NO 9
<211> LENGTH: 126
<212> TYPE: PRT
<213> ORGANISM: Cavia porcellus

<400> SEQUENCE: 9

Met Glu Leu Ala Leu Ser Trp Val Phe Leu Phe Thr Leu Leu Arg Gly
1               5                   10                  15

Val Gln Ala Glu Glu Gln Leu Val Glu Ser Gly Gly Gly Leu Val Gln
            20                  25                  30

Pro Gly Gly Ser Leu Lys Leu Ser Cys Leu Ala Ser Gly Phe Ile Phe
        35                  40                  45

Ser Ser Tyr Ala Met Asn Trp Val Arg Gln Ala Pro Gly Lys Gly Leu
    50                  55                  60

Glu Trp Ile Ser Ala Ile Ser Arg Ser Asp Ser Asn Arg Tyr Tyr Thr
65                  70                  75                  80

Asp Ser Val Lys Gly Arg Phe Thr Ile Ser Arg Asp Asp Gly Thr Asn
                85                  90                  95

Thr Leu Tyr Leu Gln Met Ser Ser Leu Arg Pro Glu Asp Thr Ala Val
            100                 105                 110

Tyr Tyr Cys Ser Arg Tyr Arg Asp Tyr Tyr Ala Leu Asp Ile
        115                 120                 125

<210> SEQ ID NO 10
<211> LENGTH: 122
<212> TYPE: PRT
<213> ORGANISM: Cavia porcellus

<400> SEQUENCE: 10

Met Arg Ile Pro Val His Leu Leu Gly Leu Leu Leu Leu Trp Ile Thr
1               5                   10                  15

Gly Ser Thr Gly Asp Val Val Met Thr Gln Thr Pro Leu Ser Leu Ser
            20                  25                  30

Val Ser Pro Gly Glu Pro Ala Ser Ile Ser Cys Arg Ala Ser Gln Ser
        35                  40                  45

Leu Leu His Ser Asn Gly Lys Thr Tyr Leu His Trp Val Val His Lys
    50                  55                  60

Pro Gly Gln Ala Pro Arg Gly Met Ile Phe Arg Val Ser Asn Lys Tyr
65                  70                  75                  80

Ser Gly Thr Pro Glu Arg Phe Ser Gly Ser Gly Ser Gly Thr Asp Phe
                85                  90                  95

Thr Leu Lys Ile Ser Arg Val Glu Ala Glu Asp Ala Gly Val Tyr Tyr
            100                 105                 110

Cys Phe Gln Asn Thr His Pro Pro Leu Thr
        115                 120

<210> SEQ ID NO 11

```
<211> LENGTH: 8
<212> TYPE: PRT
<213> ORGANISM: Cavia porcellus

<400> SEQUENCE: 11

Gly Phe Thr Phe Ser Asn Tyr Phe
1               5

<210> SEQ ID NO 12
<211> LENGTH: 8
<212> TYPE: PRT
<213> ORGANISM: Cavia porcellus

<400> SEQUENCE: 12

Ile Ser Gly Asp Ser Ser Asn Ile
1               5

<210> SEQ ID NO 13
<211> LENGTH: 11
<212> TYPE: PRT
<213> ORGANISM: Cavia porcellus

<400> SEQUENCE: 13

Thr Arg Leu Met Val Val Thr His Leu Asp Ile
1               5                   10

<210> SEQ ID NO 14
<211> LENGTH: 12
<212> TYPE: PRT
<213> ORGANISM: Cavia porcellus

<400> SEQUENCE: 14

Gln Ser Leu Leu Tyr Ser Arg Asn Asn Lys Asn Leu
1               5                   10

<210> SEQ ID NO 15
<211> LENGTH: 3
<212> TYPE: PRT
<213> ORGANISM: Cavia porcellus

<400> SEQUENCE: 15

Trp Ala Ser
1

<210> SEQ ID NO 16
<211> LENGTH: 10
<212> TYPE: PRT
<213> ORGANISM: Cavia porcellus

<400> SEQUENCE: 16

Trp Gln Gly Ile Ser Ala Pro Asn Thr Gly
1               5                   10

<210> SEQ ID NO 17
<211> LENGTH: 126
<212> TYPE: PRT
<213> ORGANISM: Cavia porcellus

<400> SEQUENCE: 17

Met Glu Leu Ala Leu Ser Trp Val Phe Leu Leu Phe Ile Leu Lys Gly
1               5                   10                  15

Val Gln Ala Asp Val Gln Leu Val Glu Ser Gly Gly Gly Leu Val Gln
            20                  25                  30

Pro Gly Gly Ser Leu Arg Leu Ser Cys Val Ala Ser Gly Phe Thr Phe
```

```
                35                  40                  45
Ser Asn Tyr Phe Met Tyr Trp Val Arg Gln Ala Pro Gly Lys Gly Leu
    50                  55                  60

Glu Trp Leu Ala Ala Ile Ser Gly Asp Ser Ser Asn Ile Lys Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Ser Ser Leu Arg Thr Glu Asp Thr Ala Val
            100                 105                 110

Tyr Tyr Cys Thr Arg Leu Met Val Val Thr His Leu Asp Ile
            115                 120                 125

<210> SEQ ID NO 18
<211> LENGTH: 117
<212> TYPE: PRT
<213> ORGANISM: Cavia porcellus

<400> SEQUENCE: 18

Met Leu Leu Thr Val Leu Leu Trp Val Ser Gly Val Cys Gly Asp Ile
1               5                   10                  15

Val Met Thr Gln Ser Pro Val Ser Leu Ile Val Ser Pro Gly Glu Ser
                20                  25                  30

Ala Thr Ile Arg Cys Gln Ser Ser Gln Ser Leu Leu Tyr Ser Arg Asn
            35                  40                  45

Asn Lys Asn Leu Leu Asn Trp Tyr Gln Gln Lys Pro Gly Gln Ser Pro
    50                  55                  60

Lys Leu Leu Ile Tyr Trp Ala Ser Thr Arg Thr Ser Gly Ile Pro Glu
65                  70                  75                  80

Arg Phe Ser Gly Ser Gly Ser Gly Thr Ala Phe Thr Leu Thr Ile Ser
                85                  90                  95

Gly Ala Gln Ala Glu Asp Val Ala Thr Tyr Tyr Cys Trp Gln Gly Ile
            100                 105                 110

Ser Ala Pro Asn Thr
            115
```